(12) United States Patent
Botti et al.

(10) Patent No.: US 7,781,488 B2
(45) Date of Patent: Aug. 24, 2010

(54) POST-CLEAVAGE SULFUR DEPROTECTION FOR CONVERGENT PROTEIN SYNTHESIS BY CHEMICAL LIGATION

(75) Inventors: Paolo Botti, Geneva (CH); Matteo Villain, Nyon (CH); Sonia Manganiello, Ferney-Voltaire (FR); Hubert Gaertner, Archamp (FR)

(73) Assignee: Amylin Pharmaceuticals, Inc., San Diego, CA (US)

( * ) Notice: Subject to any disclaimer, the term of this patent is extended or adjusted under 35 U.S.C. 154(b) by 847 days.

(21) Appl. No.: 10/516,118

(22) PCT Filed: Jun. 9, 2003

(86) PCT No.: PCT/IB03/05087

§ 371 (c)(1),
(2), (4) Date: Oct. 10, 2006

(87) PCT Pub. No.: WO03/106615

PCT Pub. Date: Dec. 24, 2003

(65) Prior Publication Data

US 2007/0059792 A1    Mar. 15, 2007

Related U.S. Application Data

(60) Provisional application No. 60/387,803, filed on Jun. 10, 2002, provisional application No. 60/407,530, filed on Aug. 30, 2002.

(51) Int. Cl.
*C08H 1/00* (2006.01)
*A61K 38/00* (2006.01)

(52) U.S. Cl. .................. 514/712; 514/127; 530/402; 530/334

(58) Field of Classification Search .................. None
See application file for complete search history.

(56) References Cited

U.S. PATENT DOCUMENTS

2002/0132975 A1* 9/2002 Canne et al. .............. 530/324

OTHER PUBLICATIONS

Muir et al. (1997) Protein synthesis by chemical ligation of unprotected peptides in aqueous solution, Meth. Enzymol., vol. 289, pp. 266-298.*
Dawson et al. (1997) Modulation of Reactivity in Native Chemical Ligation through the Use of Thiol Additives, J. Am. Chem. Soc., vol. 119, pp. 4325-4329.*
Tam et al. (1999) Orthogonal ligation strategies for peptide and protein, Biopolymers, vol. 51, No. 1, pp. 311-332.*

* cited by examiner

*Primary Examiner*—Anand U Desai
*Assistant Examiner*—Samuel Liu

(57) ABSTRACT

The present invention provides a method and compositions for synthesizing an oligopeptide or polypeptide by convergent assembly of a plurality of pairs of oligopeptides in chemical ligation reactions. An important aspect of the present invention is an oligopeptide having a C-terminal disulfide-protected carboxythioester group that can be deprotected to spontaneously generate a free C-terminal thioester moiety. This allows a single precursor to participate in a succession of chemical ligation reactions, thereby making the convergent synthesis approach possible. The present invention is useful in methods for chemical synthesis of oligopeptides, polypeptides and proteins, and improves the efficiency of native chemical ligation reactions, particularly where four or more peptide fragments are used to assemble an oligopeptide, polypeptide or protein product.

11 Claims, 20 Drawing Sheets

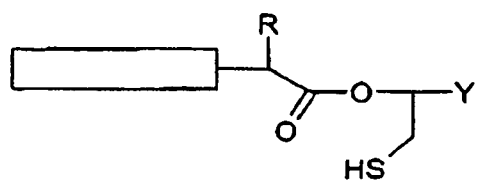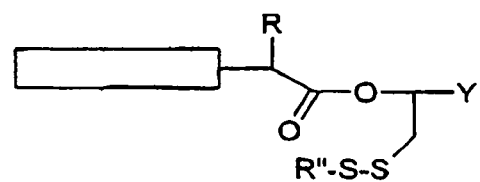
Fig 1a                              Fig 1b
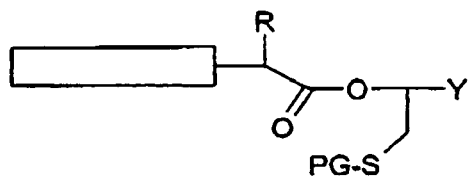
Fig 1c
Figure 1

ABCD

PG=Protecting Group

▷ Thioester (active form)

◯ Thioester precursor (inactive form) =

PG-S= Sulfur protecting group, including but not limited to disulfide moieties

⤳ n-Terminal Protected Cysteine or 1-2, 1-3 n-Terminal Protected amino thiol

> n-Terminal Cysteine, or n-Terminal 1-2, 1-3 amino thiol

SCHEME 1

SCHEME 2

SCHEME 3

Figure 8a: T=0
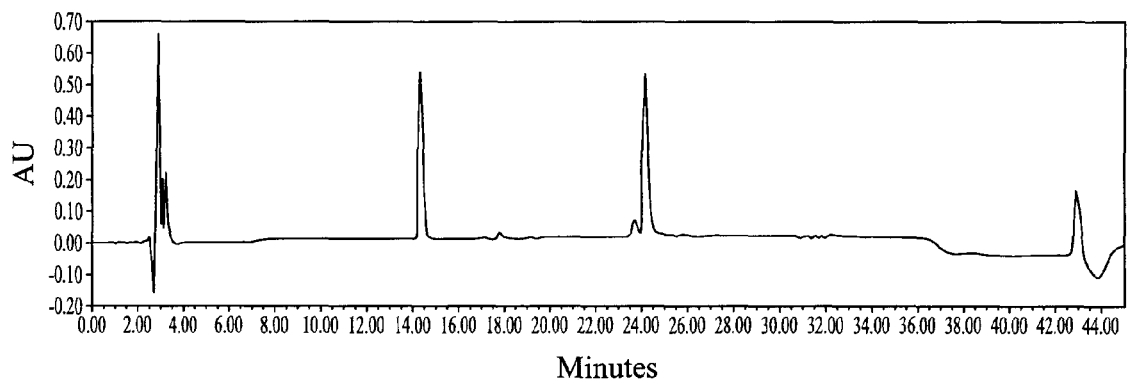
Figure 8b: T=1 h
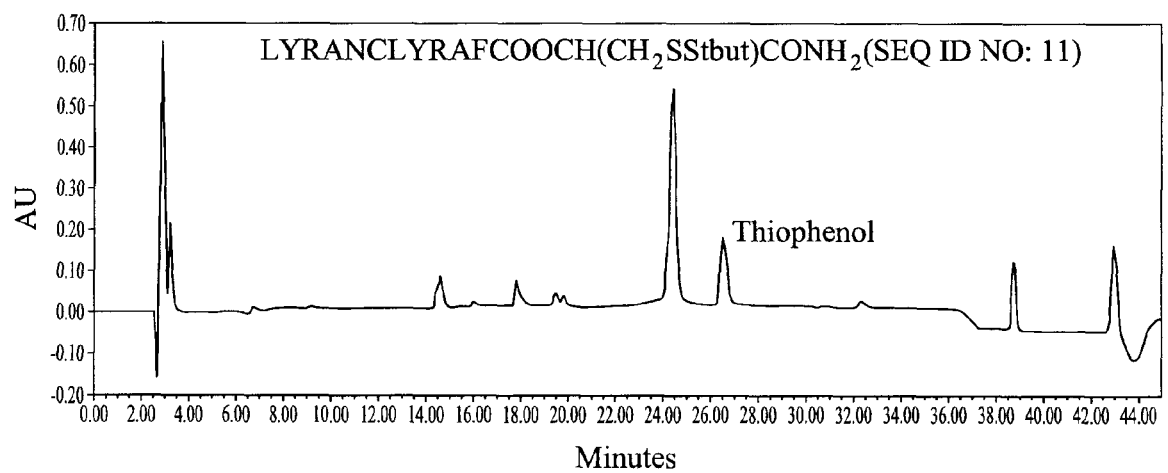
LYRANCLYRAFCOOCH(CH$_2$SStbut)CONH$_2$(SEQ ID NO: 11)
Thiophenol

Figure 8c: OVERLAY
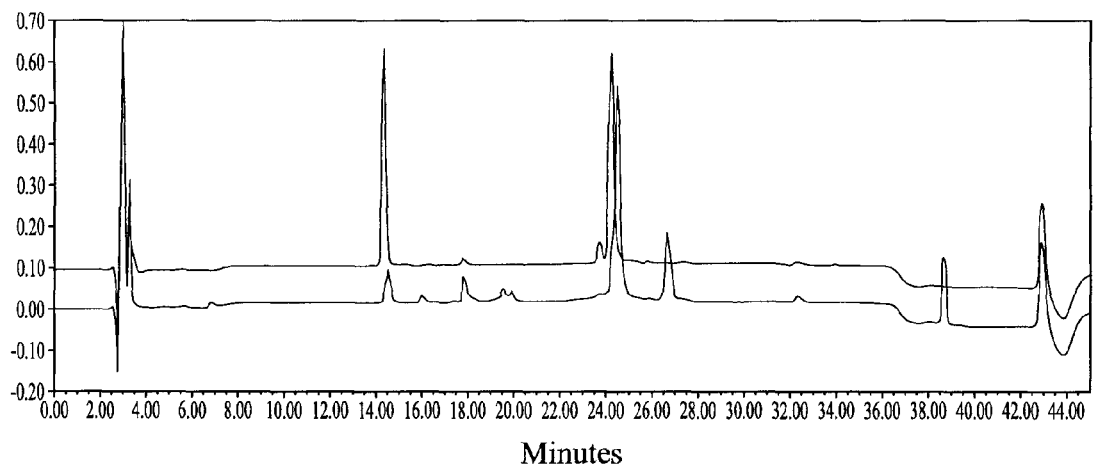
Figure 8d
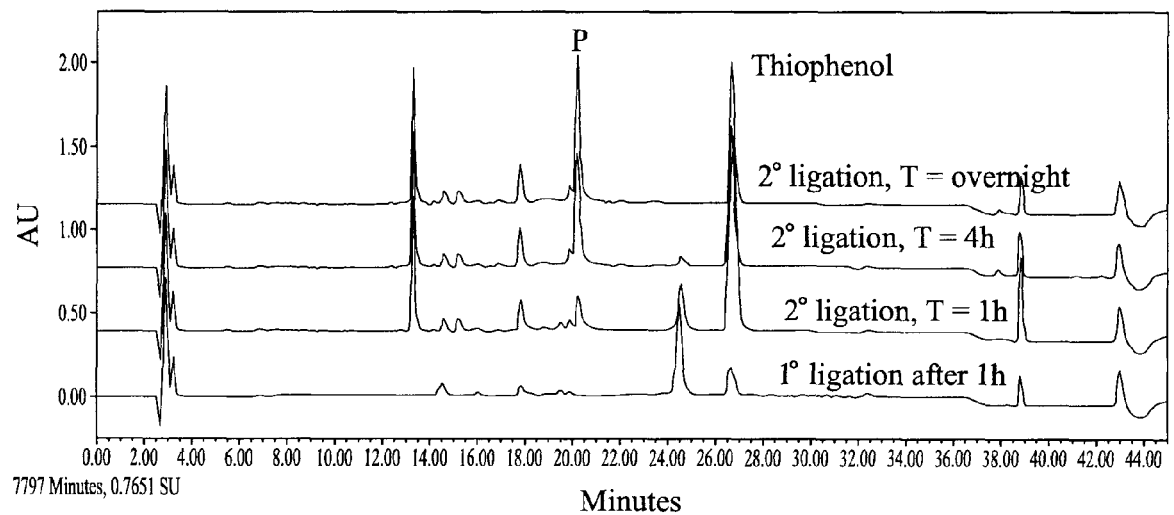
P = 3 fragments ligated product, LYRAN-CLYRAF-CYAKYAKL (SEQ ID NO: 12)

HPLC Crude of Cleavage of LYRAF(SStbut)

Peaks of the two isomers: isomer 1, 68.5% and isomer 2, 31.5% in relative abundance ratio.

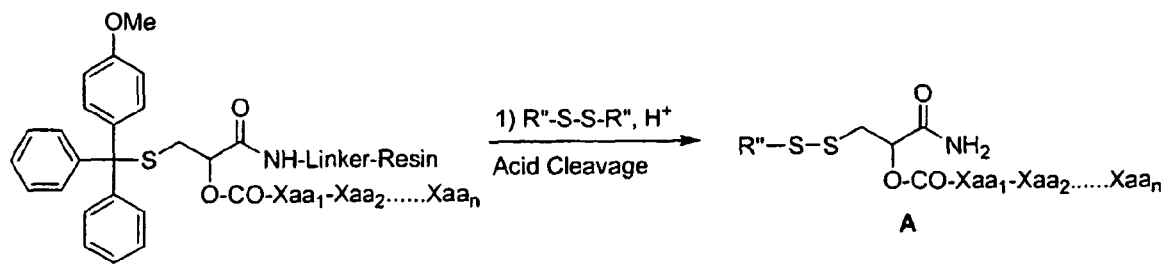
Fig. 10A
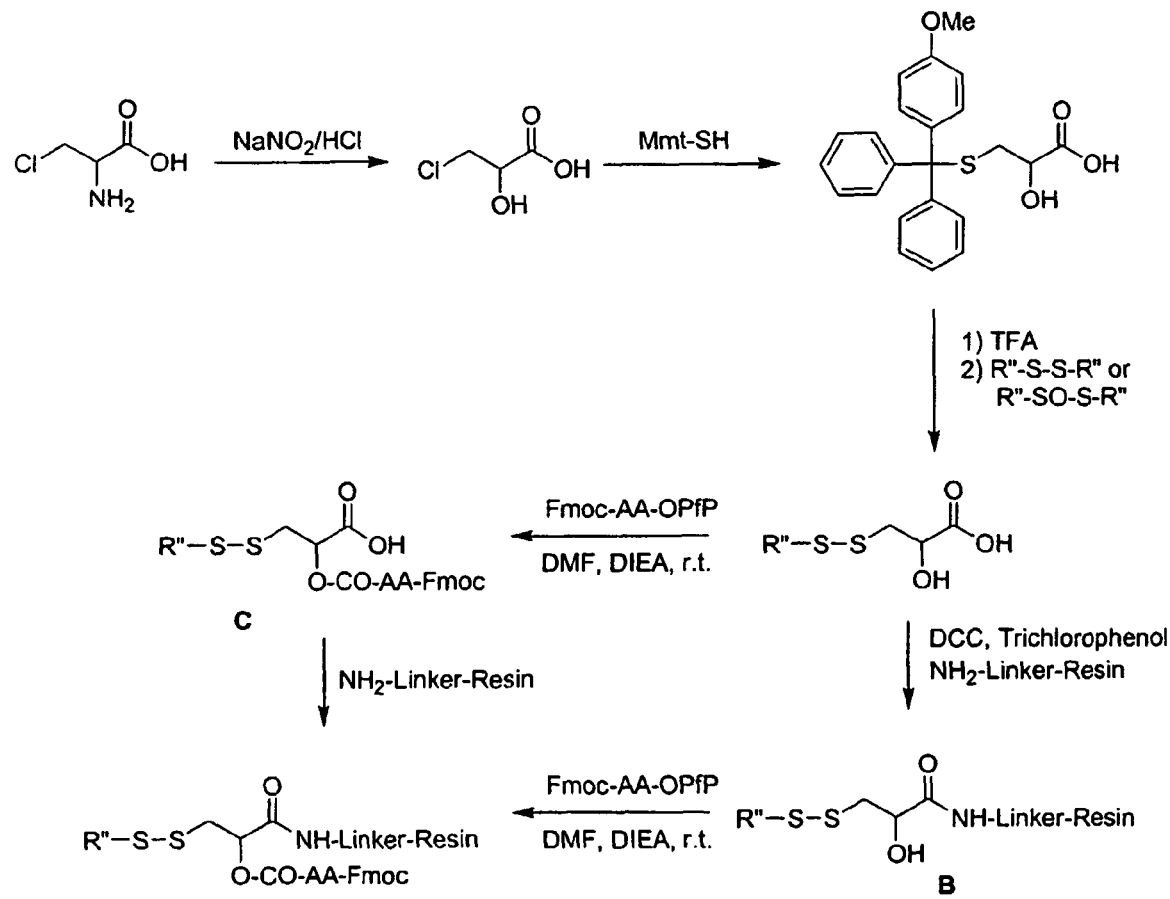
Fig. 10 B,C

A = unreacted CYAKYAKL (SEQ ID NO: 6)

B = LYRAF-COOH (SEQ ID NO: 1)

LYRAG(SStbut) (SEQ ID NO: 2) + CYAKYAKL (SEQ ID NO: 6)
Figure 12a: T=0
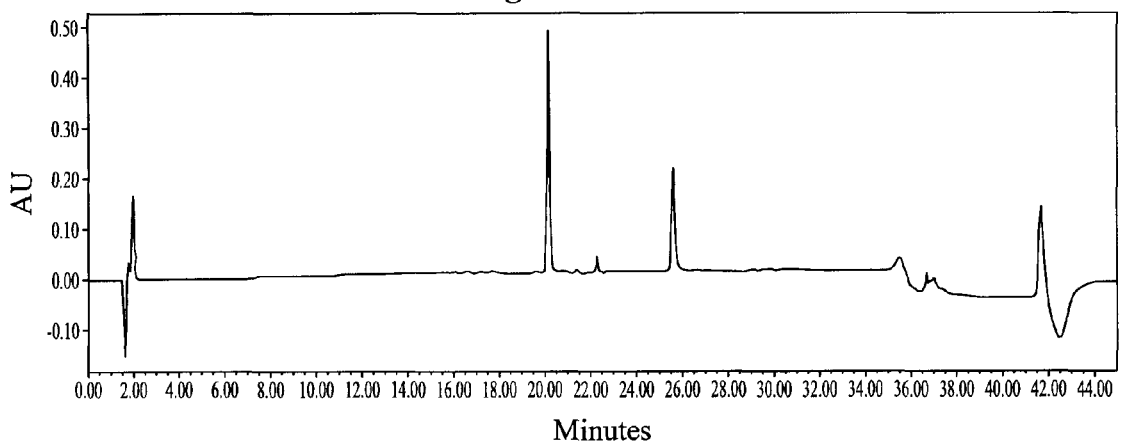
Figure 12b: overnight: Thiophenol
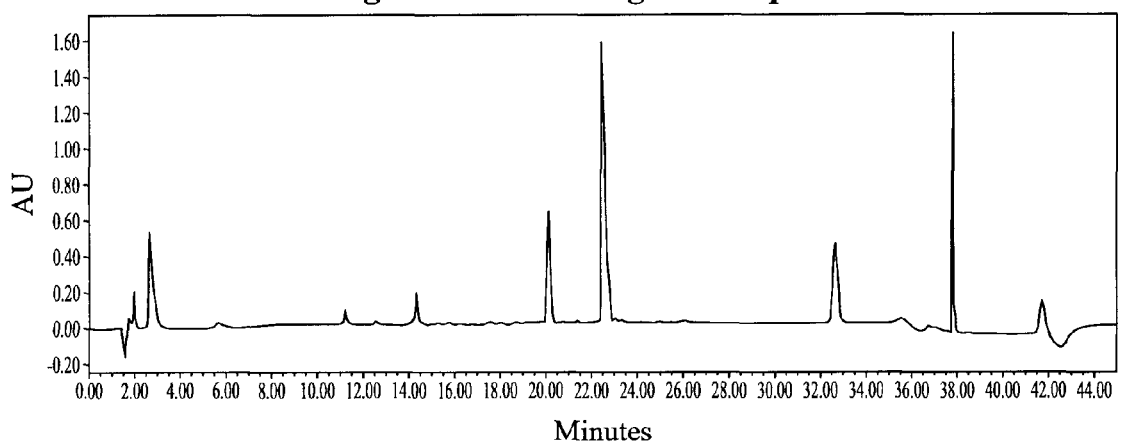
Figure 12c: overnight: thiophenol+Benzylmercaptan
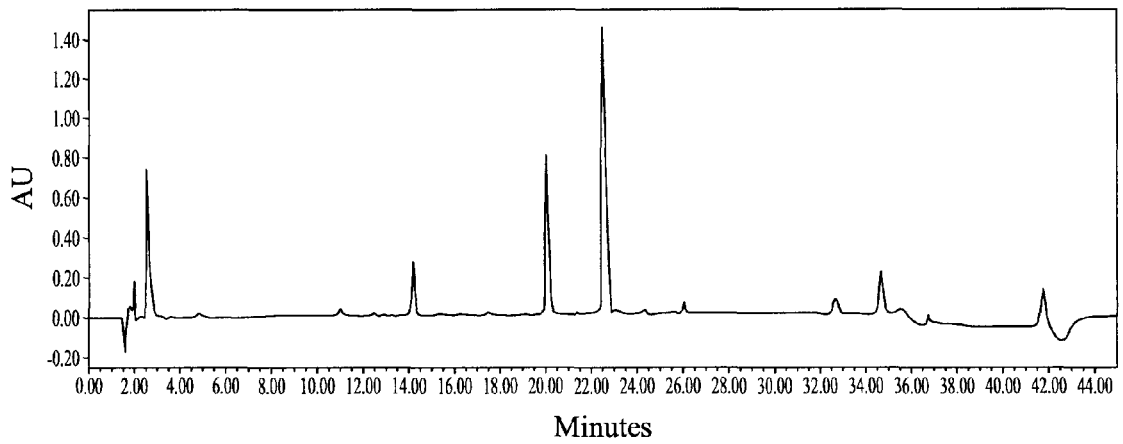

Figure 12d: Overnight: Thiophenol + tributylphosphine

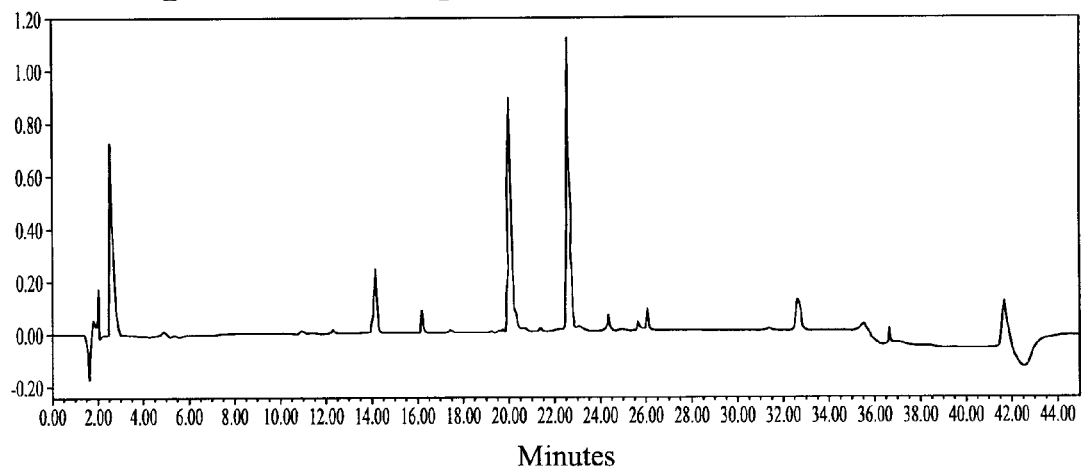

Figure 12e: Overlay

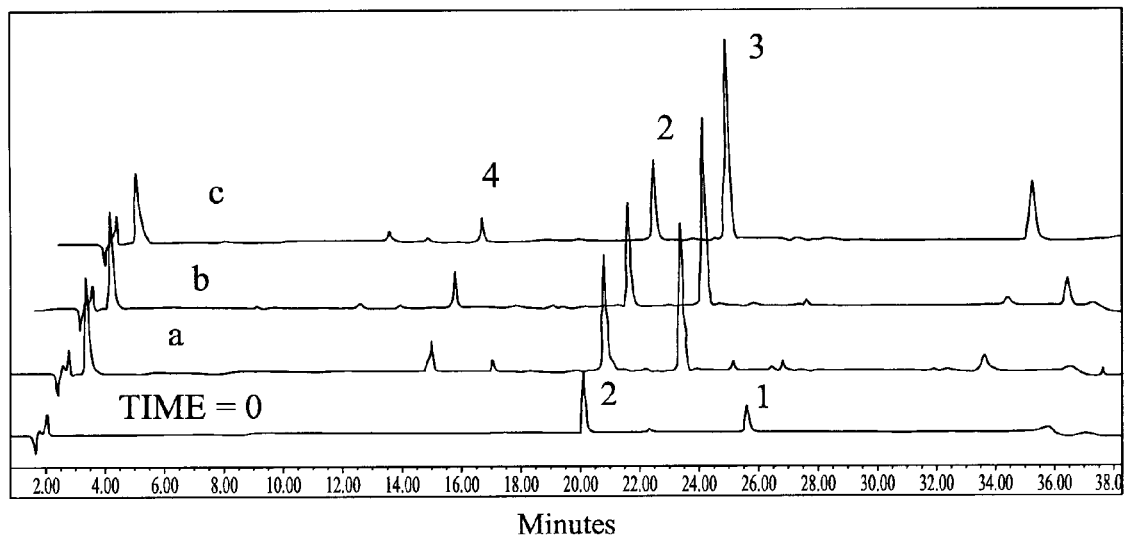

Overlay Ligation of LYRAG-CαOO-CH(CH$_2$-SStbut)-CONH$_2$ (SEQ ID NO: 2) with peptide CYAKYAKL (SEQ ID NO: 6) after 4hrs incubation
a) Ligation with 2% Thiophenol and 2% TributylPhosphine pH 6.5
b) Ligation with 2% Thiophenol 1% Benzylmercaptan pH 6.5
c) Ligation with 2% Thiophenol pH 6.5
1 = LYRAG-CαOO-CH(CH$_2$-SStbut)-CONH$_2$ (SEQ ID NO: 2)
2 = CYAKYAKL (SEQ ID NO: 6) peptide
3 = Ligation Product LYRAGCYAKYAKL (SEQ ID NO: 14)
4 = LYRAG-CαOOH (SEQ ID NO: 2)

Figure 13: Chemical Ligation to obtain NNY-Rantes 1-68
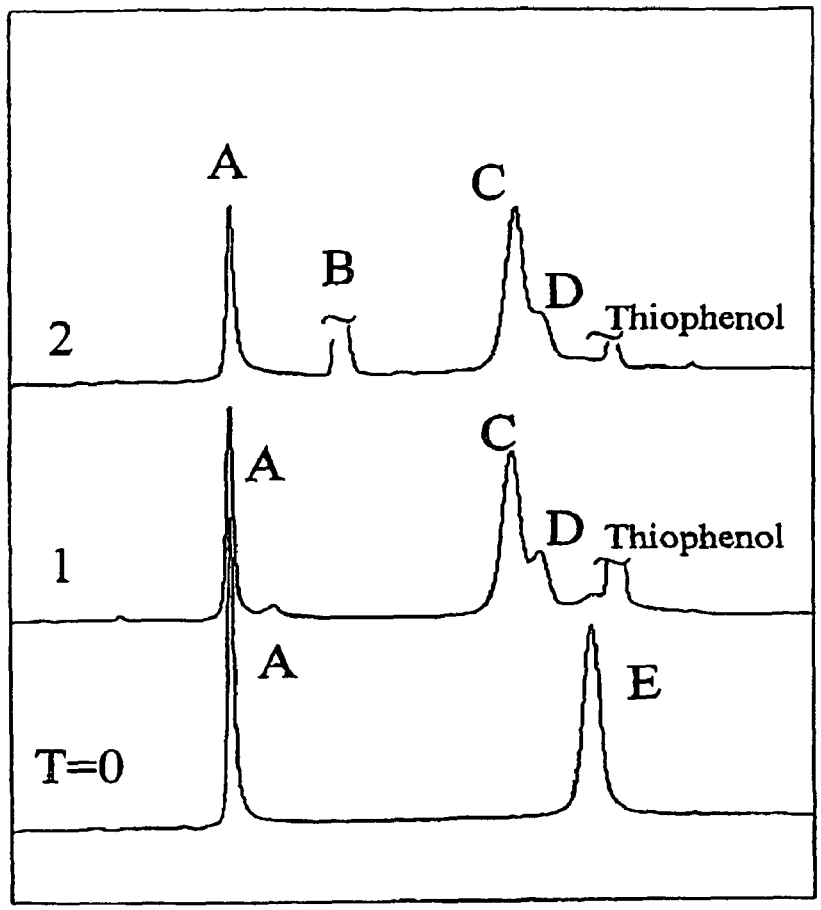
Reaction 1= TributhylPhosphine and 2%Thiophenol at after 2.5h
Reaction 2= 2%Thiophenol after 16hrs
A= C-terminal Rantes (34-68)
B= non peptidic material
C= Ligation Product, full length NNY-Rantes
D= NNY-Rantes (1-33)-COOH
E= NNY-Rantes (1-33)-COO-CH(CH$_2$-S-S-Tbut)-CONH$_2$

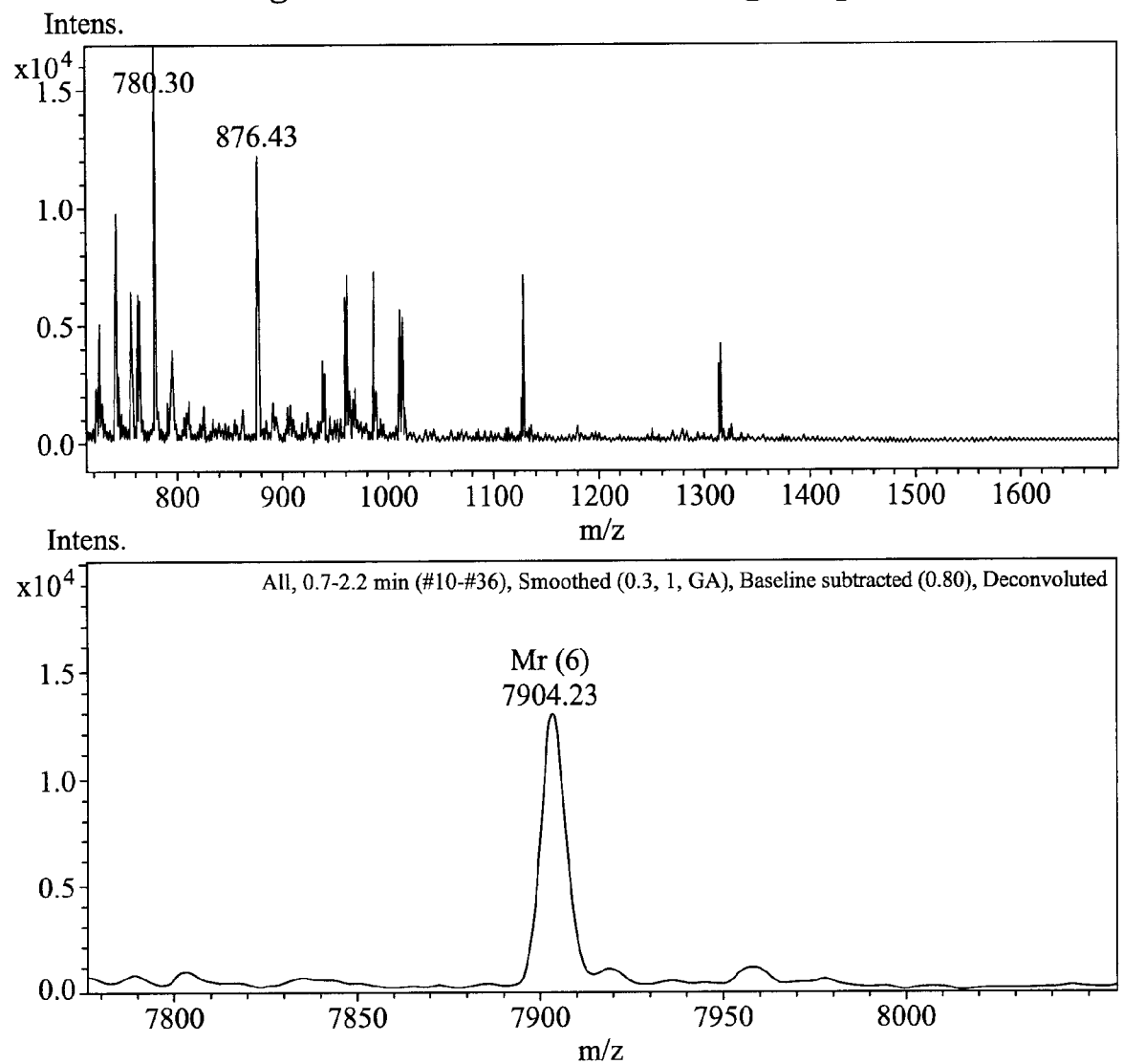
Figure 14: MS of NNY-Rantes ligated product

Figure 15: RP-HPLC analysis of chemical ligation of SPT1 1-54.
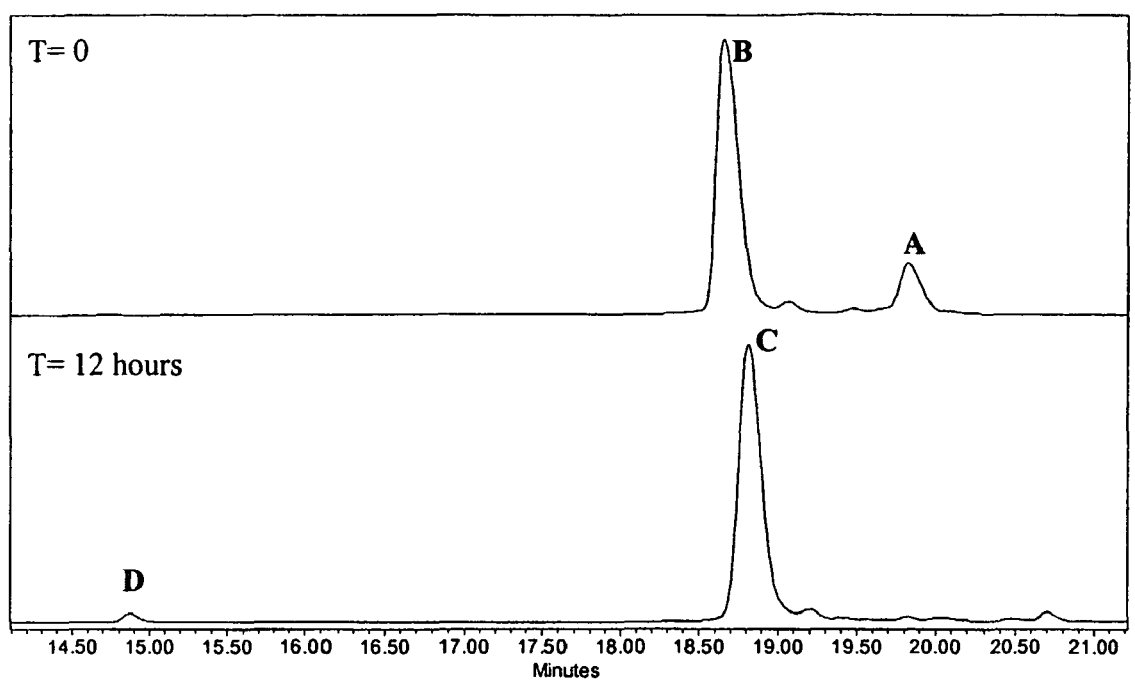
Products confirmed by mass spectroscopy:
A= fragment 1
B= fragment 2
C= non resolved mixture of fragment 2 and ligated product
D= hydrolyzed fragment 1.

Figure 16: Size exclusion chromatography analysis of chemical ligation of SPT1 1-54.
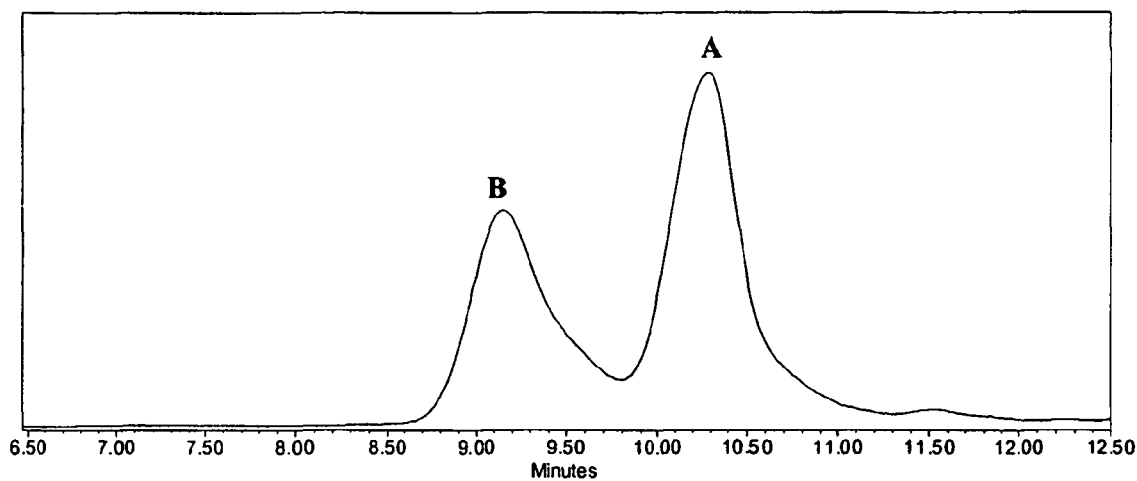
Product confirmed by mass spectroscopy:
A= fragment 2.
B= ligated product, eg. full length serine 8 phosphorylated SPT1.

Figure 17: MS analysis of purified serine 8 phosphorylated SPT1.
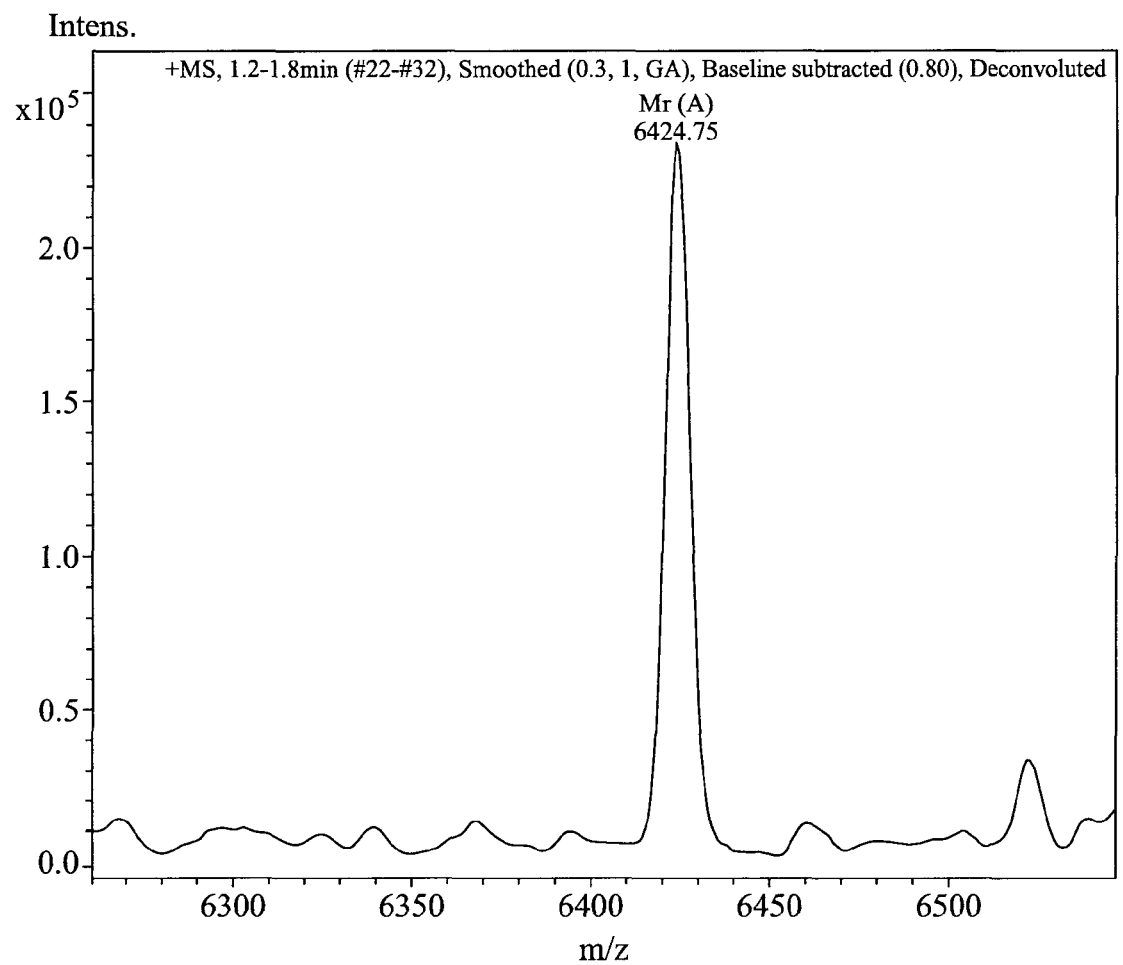
Theoretical mass: 6424.35.
Experimental mass: 6424.75.

US 7,781,488 B2

POST-CLEAVAGE SULFUR DEPROTECTION FOR CONVERGENT PROTEIN SYNTHESIS BY CHEMICAL LIGATION

CROSS-REFERENCES TO RELATED APPLICATIONS

This application claims benefit of priority to U.S. Provisional Patent Application No. 60/387,803, filed Jun. 10, 2002, and U.S. Provisional Patent Application No. 60/407,530, filed Aug. 30, 2002.

REFERENCE TO A "SEQUENCE LISTING," A TABLE, OR A COMPUTER PROGRAM LISTING APPENDIX SUBMITTED ON A COMPACT DISK

A paper copy of the Sequence Listing and a computer readable form of the sequence listing in .txt format containing the file name "Seq Listing 0950USUT TXT", which is 4.08 KB in size, filed on Oct. 19, 2009, are hereby incorporated by reference.

BACKGROUND OF THE PRESENT INVENTION

The sequencing of the human genome has created the promise and opportunity for understanding the function of all genes and proteins relevant to human biology and disease, Peltonen and McKusick, Science, 291: 1224-1229 (2001). However, several important hurdles must be overcome before this promise can be fully attained. First, even with the human genome sequence available, it is still difficult to distinguish genes and the sequences that control their expression. Second, although monitoring gene expression at the transcript level has become more robust with the development of microarray technology, a great deal of variability and control of function originates in post-transcriptional events, such as alternative splicing and post-translational processing and modification. Finally, because of the scale of human molecular biology, potentially many tens of thousands of genes, and their expression products, will have to be isolated and tested in order to understand their role in health and disease, Dawson and Kent, Annu.Rev.Biochem., 69: 923-960 (2000).

In regard to the issue of scale, the application of conventional recombinant methodologies for cloning, expressing, recovering, and isolating proteins is still a time consuming and labor-intensive process, so that its application in screening large numbers of different gene products for determining function has been limited. Recently, a synthesis approach has been developed which can address the need for facile access to highly purified research-scale amounts of protein for functional screening, Dawson and Kent (cited above) and Dawson et al., Science, 266: 776-779 (1994). In its most attractive implementation, an unprotected oligopeptide intermediate having a C-terminal thioester reacts with an N-terminal cysteine of another oligopeptide intermediate under mild aqueous conditions to form a thioester linkage which spontaneously rearranges to a natural peptide linkage, Kent et al., U.S. Pat. No. 6,184,344. The approach has been used to assemble oligopeptides into active proteins both in solution phase, e.g. Kent et al., U.S. Pat. No. 6,184,344, and on a solid phase support, e.g. Canne et al., J. Am. Chem. Soc., 121: 8720-8727 (1999). Recently, the technique has been extended to permit coupling of C-terminal thioester fragments to a wider range of N-terminal amino acids of co-reactant peptides by using a removable ethylthio moiety attached to the N-terminal nitrogen of the co-reactant, thereby mimicking the function of an N-terminal cysteine, Low et al., Proc. Natl. Acad. Sci., 98: 6554-6559 (2001).

Presently, the synthesis of oligopeptide thioesters is carried out primarily using t-butoxycarbonyl ("Boc")-based protecting groups. Alternatively, 9-fluorenylmethoxycarbonyl ("Fmoc")-based protecting groups can also be used, but only when the reaction times are short, as the nucleophilic reagants used to remove the Fmoc protecting groups also degrade the thioesters of the oligopeptides over time, as noted by Botti et al., International patent publication WO 02/18417. To address this problem, Botti et al. have suggested the use of a nucleophile-stable thioester precursor that is removable under non-nucleophilic conditions, in combination with a nucleophilic labile Fmoc protecting group as the N-terminal protecting group. While the work of Botti et al. does facilitate the coupling of amino acids and oligopeptides, the 2-mercapto carboxyesters of Botti et al. are susceptible to nucleophilic cleavage during long reaction times. As the preparation of very long oligopeptides, polypeptides and proteins requires extended reaction times, a new method that provides stable N-terminal and C-terminal protecting groups for the preparation of oligopeptides, polypeptides and proteins, would be advantageous. Surprisingly, the present invention provides such methods.

SUMMARY OF THE PRESENT INVENTION

In one aspect, the present invention provides a method for preparing an oligopeptide or polypeptide product, comprising: (a) ligating in a first reaction, first and second oligopeptides each having an N-terminus and a C-terminus, wherein the first oligopeptide comprises a C-terminus having a thioester group, and an N-terminus that is substantially unreactive with the thioester group, wherein the second oligopeptide comprises an N-terminus having an unprotected cysteine, an unprotected 1,2-amino thiol, or an unprotected 1,3-amino thiol, and a C-terminus having an inactive thioester precursor, and wherein the ligating forms a first oligopeptide ligation product comprising a C-terminus having an inactive thioester precursor, and an N-terminus that is substantially unreactive with the thioester group; (b) ligating in a second reaction, third and fourth oligopeptides each having an N-terminus and a C-terminus, wherein the third oligopeptide comprises an N-terminus having a protected cysteine, a protected 1,2-amino thiol, or a protected 1,3-amino thiol, and a C-terminus comprising a thioester, wherein the fourth oligopeptide comprises an N-terminus having an unprotected cysteine, an unprotected 1,2-amino thiol, or an unprotected 1,3-amino thiol, and a C-terminus that is substantially unreactive with the unprotected cysteine, the unprotected 1,2-amino thiol, or the unprotected 1,3-amino thiol, and wherein the ligating forms a second oligopeptide ligation product comprising an N-terminus having a protected cysteine, a protected 1,2-amino thiol, or a protected 1,3-amino thiol, and a C-terminus that is substantially unreactive with the unprotected cysteine, the unprotected 1,2-amino thiol, or the unprotected 1,3-amino thiol; (c) transforming the inactive thioester precursor of the first oligopeptide ligation product of step (a) into a thioester to form a third oligopeptide ligation product having a C-terminus comprising a thioester, and an N-terminus that is substantially unreactive with the thioester group; (d) deprotecting the N-terminus of the second oligopeptide ligation product of step (b) to form a fourth ligation product comprising an N-terminus having an unprotected cysteine, an unprotected 1,2-amino thiol, or an unprotected 1,3-amino thiol, and a C-terminus that is substantially unreactive with the unprotected cysteine, the unprotected 1,2-amino thiol, or the unprotected 1,3-amino thiol; and (e) ligating the third oligopeptide ligation product of step (c) to the fourth oligopeptide ligation product of step (d) to form a fifth oligopeptide ligation product comprising an N-terminus that is substantially unreactive with an oligopeptide bearing a C-terminal thioester group, and a C-terminus that is substantially unreactive with an oligopeptide bearing an unprotected N-terminal cysteine, an unprotected 1,2-amino thiol, or an unprotected 1,3-amino thiol.

In another aspect, the present invention provides a compound of the formula:

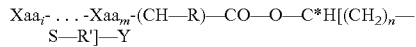
$$Xaa_i\text{-}\ldots\text{-}Xaa_m\text{-}(CH\text{—}R)\text{—}CO\text{—}O\text{—}C^*H[(CH_2)_n\text{—}S\text{—}R']\text{—}Y$$

wherein $Xaa_i$ is a protected or unprotected amino acid for i=1 to m; m is an integer from 2 to 200; n is an integer from 1 to 10; C* is a chiral carbon in either the R or the S configuration, and substantially free of the other configuration; R is an amino acid side chain; R' is a member selected from the group consisting of a sulfur protecting group, —SR" and hydrogen; R" is a member selected from the group consisting of $C_{2-10}$alkyl, substituted aryl having from 5 to 12 carbon atoms, substituted benzyl, and substituted heteroaryl having from 5 to 12 carbon atoms and 1 to 4 heteroatoms each independently selected from the group consisting of N, O and S; Y is an electron withdrawing group selected from the group consisting of $R^c$, $C_{1-3}$alkyl substituted with 1-3 $R^c$ groups, —C(O)—$R^d$, —S(O)$_p$—$C_{1-3}$alkyl substituted with 0-3 $R^c$ groups, and an aryl substituted with 1-3 $R^c$ groups; each $R^c$ group is independently a member selected from the group consisting of halogen, polyhaloalkyl, substituted or unsubstituted benzyl, substituted or unsubstituted aryl, —C(O)NH$_2$, —C(O)—NHNH$_2$, —S(O)$_2$NH$_2$, substituted and unsubstituted hydroxyl-amine, cyano, nitro and quaternary ammonium salts; p is an integer from 1 to 2; $R^d$ is a member selected from the group consisting of hydrogen, —N($R^e$)$_2$, —O$R^e$ and —S$R^e$; each $R^e$ is independently a member selected from the group consisting of hydrogen, $C_{1-3}$alkyl substituted with 0-3 $R^c$ groups, and —SO$_2$—$C_{1-3}$alkyl substituted with 1-3 $R^c$ groups; alternatively, when two $R^e$ groups are present, they can be taken together with the atom to which they are attached to form a 5-6 membered non-aromatic heterocyclic ring containing 1-3 heteroatoms each independently selected from the group consisting of N, O and S, substituted with 0-3 $R^c$ groups.

In yet another aspect, the present invention provides a compound of the formula:

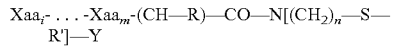
$$Xaa_i\text{-}\ldots\text{-}Xaa_m\text{-}(CH\text{—}R)\text{—}CO\text{—}N[(CH_2)_n\text{—}S\text{—}R']\text{—}Y$$

wherein $Xaa_i$ is a protected or unprotected amino acid for i=1 to m; m is an integer from 2 to 200; n is an integer from 1 to 10; R is an amino acid side chain; R' is a sulfur protecting group; Y is an electron withdrawing group selected from the group consisting of $R^c$, $C_{1-3}$alkyl substituted with 1-3 $R^c$ groups, —C(O)—$R^d$, —S(O)$_p$—$C_{1-3}$alkyl substituted with 0-3 $R^c$ groups, and an aryl substituted with 1-3 $R^c$ groups; each $R^c$ group is independently a member selected from the group consisting of halogen, polyhaloalkyl, substituted or unsubstituted benzyl, substituted or unsubstituted aryl, —C(O)NH$_2$, —C(O)—NHNH$_2$, —S(O)$_2$NH$_2$, substituted and unsubstituted hydroxyl-amine, cyano, nitro and quaternary ammonium salts; p is an integer from 1 to 2; $R^d$ is a member selected from the group consisting of hydrogen, —N($R^e$)$_2$, —O$R^e$ and —S$R^e$; each $R^e$ is independently a member selected from the group consisting of hydrogen, $C_{1-3}$alkyl substituted with 0-3 $R^c$ groups, —SO$_2$—$C_{1-3}$alkyl substituted with 1-3 $R^c$ groups; alternatively, when two $R^e$ groups are present, they can be taken together with the atom to which they are attached to form a 5-6 membered non-aromatic heterocyclic ring containing 1-3 heteroatoms each independently selected from the group consisting of N, O and S, substituted with 0-3 $R^c$ groups.

In a further aspect, the present invention provides a compound of the formula:

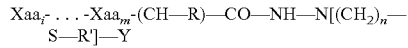
$$Xaa_i\text{-}\ldots\text{-}Xaa_m\text{-}(CH\text{—}R)\text{—}CO\text{—}NH\text{—}N[(CH_2)_n\text{—}S\text{—}R']\text{—}Y$$

wherein $Xaa_i$ is a protected or unprotected amino acid for i=1 to m; m is an integer from 2 to 200; n is an integer from 1 to 10; R is an amino acid side chain; R' is a sulfur protecting group; Y is an electron withdrawing group selected from the group consisting of $R^c$, $C_{1-3}$alkyl substituted with 1-3 $R^c$ groups, —C(O)—$R^d$, —S(O)$_p$—$C_{1-3}$alkyl substituted with 0-3 $R^c$ groups, and an aryl substituted with 1-3 $R^c$ groups; each $R^c$ group is independently a member selected from the group consisting of halogen, polyhaloalkyl, substituted or unsubstituted benzyl, substituted or unsubstituted aryl, —C(O)NH$_2$, —C(O)—NHNH$_2$, —S(O)$_2$NH$_2$, substituted and unsubstituted hydroxyl-amine, cyano, nitro and quaternary ammonium salts; p is an integer from 1 to 2; $R^d$ is a member selected from the group consisting of hydrogen, —N($R^e$)$_2$, —O$R^e$ and —S$R^e$; each $R^e$ is independently a member selected from the group consisting of hydrogen, $C_{1-3}$alkyl substituted with 0-3 $R^c$ groups, —SO$_2$—$C_{1-3}$alkyl substituted with 1-3 $R^c$ groups; alternatively, when two $R^e$ groups are present, they can be taken together with the atom to which they are attached to form a 5-6 membered non-aromatic heterocyclic ring containing 1-3 heteroatoms each independently selected from the group consisting of N, O and S, substituted with 0-3 $R^c$ groups.

BRIEF DESCRIPTION OF THE DRAWINGS

FIG. 1a-1c illustrate a carboxythioester protection group of the present invention (FIG. 1a, where n=1 and R'=H), a disulfide protected carboxythioester protection group of the present invention (FIG. 1b, where n=1 and R'=S—R") and a general protected form of the present invention (FIG. 1c, where n=1 and R'=PG).

FIG. 8a-8d illustrate an example of the use of oligopeptides of the present invention in a convergent synthesis scheme for making an oligopeptide or polypeptide product. FIG. 8a to 8d show the absorbance signal at the output of an HPLC apparatus at different times during the reaction. FIG. 8a discloses 'LYRANCLYRAF' as SEQ ID NO: 11 and FIG. 8d discloses 'LYRAN-CLYRAF-CYAKYAKL ' as SEQ ID NO 12.

FIG. 10A-10D illustrate the preparation of the disulfide protected carboxythioester groups of the present invention according to different synthetic strategies (FIGS. 10A to 10D).

FIG. 12a-12d illustrate the ligation of model Peptide LYRAG-COO—CH(CH$_2$—S—S-t-But)-CONH$_2$ (SEQ ID NO: 2) at two different times (t=0, FIG. 12a and after overnight reaction, FIG. 12b) and also under different conditions (FIGS. 12c to 12e). 'LYRAG', 'GYAKYAKL', and 'LYRAG-CYAKYAKL' are disclosed as SEQ ID NOS 2, 6 and 14, respectively.

FIG. 13 illustrates the HPLC chromatograms following the synthesis of NNY Rantes 1-68.

FIG. 14 illustrates the MS data of synthesized NNY Rantes 1-68.

FIG. 15 illustrates a RP-HPLC analysis of the chemical ligation to form SPT1 1-54 (see Example 12).

FIG. 16 shows the size exclusion chromatography analysis of chemical ligation of SPT1 1-54 (see Example 12).

FIG. 17 shows the MS analysis of purified serine 8-phosphorylated SPT1.

DETAILED DESCRIPTION OF THE PRESENT INVENTION

I. Definitions

Figure 2:
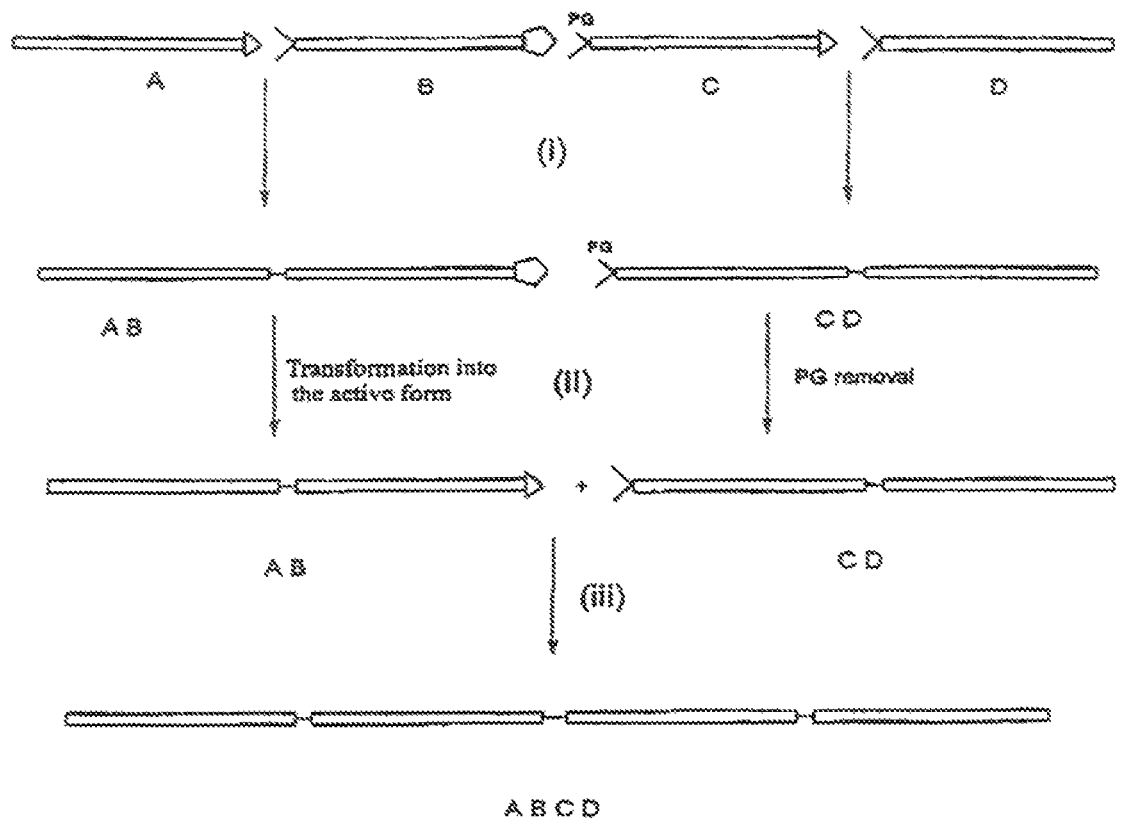
FIG. 2 illustrates the use of oligopeptides of the present invention in a convergent synthesis scheme for making an oligopeptide or polypeptide product.
Figure 2:
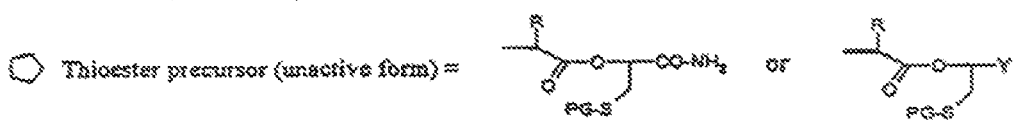

As used herein, the terms "peptide," "peptide fragment," "oligopeptide," or "fragment" in reference to a peptide are used synonymously and refer to a compound made up of a single unbranched chain of amino acid residues linked by peptide bonds. Amino acid residues are sometimes represented herein by the symbol "Xaa$_i$," where "i", when present, designates the position of the amino acid within a peptide. Each Xaa$_i$ is independently selected from the group of natural and non-natural amino acids. Amino acids in a peptide or oligopeptide can be derivatized with lipid moieties, polyethylene glycol, dyes, biotin, haptens, oligonucleotides, or like moieties. The number of amino acid residues in such compounds varies widely. Peptides or oligopeptides referred to herein preferably have from 2 to 70 amino acid residue. More preferably, peptides or oligopeptides referred to herein have from 2 to 50 amino acid residues.

As used herein, the term "protein" is used synonymously with the term "polypeptide", or can refer to, in addition, a complex of two or more polypeptides which can be linked by bonds other than peptide bonds, for example, such polypeptides making up the protein can be linked by disulfide bonds. The term "protein" can also include a family of polypeptides having identical amino acid sequences but different post-translational modifications, such as phosphorylations, acylations, glycosylations, and the like. In particular, these post-translational modifications can be added when such proteins are expressed in eukaryotic hosts. Polypeptides and proteins referred to herein usually have from a few tens of amino acid residues, e.g. 20, to up to a few hundred amino acid residues, e.g. 200, or more.

Amino acid residues are referred to herein by their standard single-letter or three-letter notations: A, alanine; C, cysteine; D, aspartic acid; E, glutamic acid; F, phenylalanine; G, glycine; H, histidine; I, Isoleucine; K, lysine; L, leucine; M, methionine; N, asparagine; P, proline; Q, glutamine; R, arginine; S, serine; T, threonine; V, valine; W, tryptophan; and Y, tyrosine. An amino acid sequence set forth herein, such as "DKLLM (SEQ ID NO: 3)," orders the amino acids from the N-terminus to the C-terminus in a left-to-right manner, unless otherwise indicated from the context. One of skill in the art will appreciate that non-natural amino acids are also useful in the present invention.

As used herein, "electron withdrawing" refers to the tendency of a substituent to attract valence electrons from the molecule to which it is attached, i.e. it is electronegative, and "electron donating" refers to the tendency of a substituent to donate valence electrons to the molecule to which it is attached, i.e. it is electropositive, e.g., Smith and March, March's Advanced Organic Chemistry: Reactions, Mechanisms, Structure, 5$^{th}$ Edition (Wiley-Interscience, New York, 2001). Preferred electron withdrawing substituents are halogen, substituted or unsubstituted amides, substituted or unsubstituted sulfonamides, substituted or unsubstituted benzyl, substituted or unsubstituted hydroxy-amine, polyhaloalkyl, hydrazide, cyano, nitro and quaternary ammonium salts, or alkyl groups having 1 to 3 carbons and substituted with one or more of the above substituents, aryl groups substituted with one or more of the above substituents, substituted or unsubstituted esters, or substituted or unsubstituted thioesters. More preferably, electron withdrawing substituents are halo-substituted methyl. Preferred electron donating substituents include alkyl having from 1 to 3 carbon atoms, methoxy, thiol, hydroxyl, and methylthio. More preferably, electron donating substituents are methoxy, thiol, methylthio, or hydroxyl. Preferably, whenever a substituent is substituted with an electron-donating group or an electron-withdrawing group, such as electron donating- or electron-withdrawing-substituted phenyl, between 1 and 3 such groups are attached. More preferably, between 1 and 2 such groups are attached.

As used herein, the term "chemically ligating" refers to the joining of two oligopeptides to form a single product, such as another oligopeptide, a polypeptide, or a protein, for example.

As used herein, the term "transforming" refers to the transformation of a first chemical moiety to a second chemical moiety. In a preferred embodiment, the transformation from the first chemical moiety to the second proceeds through at least one intermediate.

As used herein, the term "inactive thioester precursor" refers to a chemical moiety that, upon transformation, affords an active thioester moiety.

As used herein, the term "ligation products" refers to products formed through the chemical ligation of oligopeptides.

An alkyl group is branched or unbranched and contains 1 to 7 carbon atoms, preferably 1-4 carbon atoms. Alkyl represents, for example, methyl, ethyl, propyl, butyl, isopropyl or isobutyl. Alkyl groups can be substituted by up to 3 substituents selected from alkoxy, aryl, heterocyclyl, hydroxy, halogen, cyano, optionally substituted amino, optionally substituted amino-oxy- or trifluoromethyl.

Aryl represents a monocyclic, bicyclic or tricyclic aromatic ring system, for example, phenyl or phenyl mono-, di- or tri-substituted by one, two or three radicals independently selected from alkyl, alkoxy, unsubstituted phenyl, hydroxy, halogen, cyano, amino, amino-alkyl, trifluoromethyl, alkylenedioxy and oxy-C$_2$-C$_3$-alkylene, all of which are optionally further substituted, for instance as hereinbefore defined. Aryl can also represent 1- or 2-naphthyl, or 1- or 2-phenanthrenyl.

Preferred as aryl is naphthyl, phenyl or phenyl mono- or disubstituted by alkoxy, halogen, alkyl or trifluoromethyl, especially phenyl or phenyl-mono- or disubstituted by alkoxy, halogen or trifluoromethyl, and in particular phenyl.

Representative examples of substituted phenyl groups are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl and 4-(2-methoxyethylaminomethyl)-phen-1-yl.

Benzyl represents a phenyl-CH$_2$— group. Substituted benzyl means a benzyl group in which the phenyl ring is substituted with one or more ring system substituents. Representative benzyl groups include 4-bromobenzyl, 4-methoxybenzyl, 2,4-dimethoxybenzyl, and the like.

The term "heteroaryl" refers to a monocyclic or bicyclic aromatic ring system having 5-12 carbons and 1-4 ring members as heteroatoms each independently selected from N, O and S. Representative examples include pyridyl, indolyl, indazolyl, quinoxalinyl, quinolinyl, isoquinolinyl, benzothienyl, benzofuranyl, benzopyranyl, benzothiopyranyl, furanyl, pyrrolyl, thiazolyl, benzothiazolyl, oxazolyl, isoxazolyl, triazolyl, tetrazolyl, pyrazolyl, imidazolyl, and thienyl, each of which is optionally substituted, preferably mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, and indazolyl, each of which is optionally substituted, preferably mono- or di-substituted.

Biaryl may preferably be, e.g., biphenyl, namely 2, 3 or 4-biphenyl, preferably, 4-biphenyl, each optionally substituted by, e.g., alkyl, alkoxy, halogen, trifluoromethyl or cyano, or heterocyclic-carbocyclic biaryl, preferably, e.g., thienylphenyl, pyrrolylphenyl and pyrazolylphenyl.

Amino can be optionally substituted by, e.g., alkyl.

Heterocyclyl represents a saturated cyclic hydrocarbon containing one or more, preferably 1 or 2, hetero atoms selected from O, N or S, and from 3 to 10, preferably 5 to 8, ring atoms. For example, tetrahydrofuranyl, tetrahydrothienyl, tetrahydropyrrolyl, piperidinyl, piperazinyl or morpholino; all of which can be optionally substituted, for instance as hereinbefore defined for aryl.

Halogen (halo) preferably represents chloro or fluoro, but may also be bromo or iodo.

The term "polyhalo" defines a compound or radical which has at least two available hydrogens substituted with a halogen. Those compounds or chemical moieties that have all available hydrogens replaced with a halogen are termed "perhalo". For example, perfluorophenyl can refer to 1,2,3,4,5-pentafluorophenyl, perfluoromethane can refer to 1,1,1-trifluoromethyl, and perfluoromethoxy can refer to 1,1,1-trifluoromethoxy.

As used herein, the term "quaternary ammonium salts" refers to chemical moieties of the following formula:

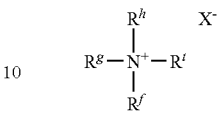

wherein $R^f$, $R^g$, $R^h$ and $R^t$ are generally hydrogen, alkyl, or aryl, or one of $R^f$, $R^g$, $R^h$ and $R^t$ can be an amino acid, a peptide, or a protein, for example, and $X^-$ is an anionic chemical moiety, such as a halogen, sulphate, nitrate, phosphate, or carbonate, that is ionically bound to the positively charged nitrogen atom.

As used herein, the term "hydroxy-amine" refers to compounds of the following structure: $N(R^{11})_2$—$OR^5$, wherein each of $R^{11}$ and $R^5$ can be hydrogen, alkyl and aryl, for example. In some embodiments, both $R^{11}$ groups can be taken together to form a double bond of the following formula: 

II. General

The present invention stems from the fact that the carboxyester structure shown in FIG. 1a with the free thiol has a limited applicability, since it is prone to hydrolysis, to generate the free carboxylic acid and therefore the effectiveness of the depicted structure depends on the size of the peptide fragments in ligation. This is crucial in the preparation of long oligopeptide and polypeptide chains where, due to the complexity of the system, the ligation is much slower than on small model peptides. Any improvement to the stability of the carboxythioester system can therefore have a very significant impact on the production yields of larger oligopeptides, polypeptides and proteins, potentially of high biological importance.

In accordance with the present invention, a solution to reduce the amount of free carboxylic acid is to keep the thiol protected during the cleavage and purification steps. Such a protection scheme presents several advantages: when the thiol is protected as, e.g., disulfide bond (S—S—R"), (FIG. 1b), the disulfide protected 2-mercapto carboxyester shows total stability under cleavage conditions, even when Lys and Phe are the adjacent amino acid residues. Moreover, purification of the intermediate is simplified since the protected thiol does not undergo isomerism due to O to S acyl-migration. Furthermore, the carboxyester with the protected thiol can be more easily differentiated from the hydrolyzed form due to the additional mass of the protecting group. Such a scheme also significantly facilitates the preparation of the S-disulfide protected 2-mercapto carboxyester intermediates. In fact, the S-disulfide protected cysteine can be coupled to a solid support using standard coupling conditions, and after removal of the amino protecting group, the free amine is then transformed into an OH moiety by reacting with $KNO_2$ in acidic conditions. At this point the resin can be functionalized with the amino acid of choice using a base-catalyzed coupling like HBTU/DIEA with DMAP (FIG. 10). Such a transformation is much more efficient when the cysteine protecting group is a disulfide rather than a general thioether. When the thiol is protected as a disulfide, the sulfur atom is in a different oxidation state than when the sulfur is in a thioether. The sulfur in the disulfide bond is therefore more stable than the sulfur in thioether. The carboxy thioester with thiol protected as disulfide (FIG. 1b) can be easily cleaved, purified and stored.

In order to use such a carboxy thioester, a free active thiol can be liberated in situ under ligation conditions by adding: (i) thiols to catalyze the ligation (e.g. thiophenol); and/or (ii) phosphine, (TCEP or Pbut$_3$) or any other reducing agent compatible with ligation, such as sodium dithionite. The in situ generated active thiol undergoes rapid isomerization to generate a desired thioester for the chemical ligation reaction.

This strategy is especially advantageous when the disulfide pair is made with S—S-tert-butyl (sulfur protected as S-tert-butylthio). Indeed, due to the high steric hindrance of the tert-butylthio moiety, the cleavage of the disulfide is much slower than on a standard disulfide pair under similar conditions. In such a situation, the free active thiol is liberated slowly, allowing a strong excess of the N-terminal cysteine or the 1,2- or 1,3-N-terminal amino thiol fragment to be present, and thus driving the process to completion with higher yield. This positive effect of the S—S-tert-butyl protection scheme (i.e. a reduction of the hydrolyzed carboxyester during ligation) could in theory be mimicked by using the unprotected 2-mercapto carboxyesters derivatives with a stronger excess of the N-terminal cysteine fragment. This, however, would require a significant amount of the excess of N-terminal cysteine fragment to be wasted, thus rendering the process more inefficient.

Furthermore, such a protection with S—S-tert-butyl (sulfur protected as S-tert-butylthio) can be exploited as a protecting strategy in a convergent or multi-step synthesis. A peptide fragment bearing at the N-terminal a free cysteine and at the C-terminal a S-tert-butylthio carboxyester, can selectively undergo native chemical ligation with an incoming thioester fragment using either a mild reducing agent or a mild nucleophile. A mild reducing agent, such as a phosphine like TCEP or PBut$_3$, would be useful as it does not reduce the S—S-tert-butyl moiety very rapidly. Furthermore, a mild nucleophile, like thiophenol or sodium dithionite, both in stoichiometric amount or in low excess, would be useful as both act without significantly cleaving the S—S-tert-butyl protecting group. Following completion of the first ligation, the deprotection of the S—S-tert-butyl moiety occurs. Simply by adding in the same reaction mixture a third fragment with an N-terminal free cysteine or a 1,2- or 1,3-amino thiol, along with a stronger excess of reducing agent or of a nucleophile, the chemical ligation with the third fragment occurs, thereby permitting the N to C synthesis (FIG. 2).

With such a strategy, a three segment ligation synthesis can be sequentially performed in the same reaction mixture, without intermediate purifications, thereby making the process faster, easier and more efficient without subsequent loss of material during purification steps (FIG. 8).

Moreover, because of the steric hindrance and the physical properties of the bulky S—S-tert-butyl group, separation of the two diastereomers generated during synthesis is facilitated, since these have different stability and reactivity during ligation. It is therefore possible to isolate and employ in the ligation scheme of the present invention the most stable structure of the two. This results in a lower amount of hydrolyzed carboxylic acid, thus enhancing the efficiency of the whole process (Example 9 and FIG. 9).

FIG. 2 demonstrates a scheme for the convergent strategy for chemically ligating peptide fragments to prepare the oligopeptide and polypeptide products of the present invention. In FIG. 2, there are two pairs of oligopeptides, A and B, and C and D, wherein each oligopeptide has an N-terminus and a C-terminus. Oligopeptide A has a thioester group at the C-terminus, and an N-terminus that is substantially unreactive to the thioester group at the C-terminus. Oligopeptide B has a cysteine or a 1,2- or 1,3-amino thiol at the N-terminus, and an inactive thioester precursor at the C-terminus. In the other pair of oligopeptides, oligopeptide C has a protected cysteine or a protected 1,2- or 1,3-amino thiol at the N-terminus, and a thioester at the C-terminus. Oligopeptide D has an unprotected cysteine or unprotected 1,2- or 1,3-amino thiol at the N-terminus, and a C-terminus that is substantially unreactive with the unprotected cysteine or unprotected 1,2- or 1,3-amino thiol. In one reaction vessel, oligopeptides A and B are chemically ligated to form the first oligopeptide ligation product (A-B), having an inactive thioester precursor at the C-terminus and an N-terminus that is substantially unreactive to the thioester group. In a separate, but parallel, reaction vessel, oligopeptides C and D are chemically ligated to form a second oligopeptide ligation product (C-D), having a protected cysteine or a protected 1,2- or 1,3-amino thiol at the N-terminus, and a C-terminus that is substantially unreactive with the unprotected cysteine or unprotected 1,2- or 1,3-amino thiol. The inactive thioester precursor of the first ligation product (A-B) is then transformed into a thioester to afford a third oligopeptide ligation product A-B*). The protected cysteine or protected 1,2- or 1,3-amino thiol of the second oligopeptide ligation product (C-D) is deprotected to afford the fourth oligopeptide ligation product (C*-D). The third (A-B*) and fourth (C*-D) oligopeptide ligation products are then placed into a single reaction vessel and are chemically ligated to form a fifth oligopeptide ligation product (A-B-C-D).

III. Methods for the Convergent Synthesis of Oligopeptides, Polypeptides and Proteins The present invention provides methods for the assembly of oligopeptides into an oligopeptide or polypeptide by the process of native chemical ligation. Related methods are described by Dawson et al., Science, 266: 776-779 (1994); Low et al., Proc. Natl. Acad. Sci., 98: 6554-6559 (2001) and Botti et al., Tetrahedron Letters, 42: 1831-1833 (2001). In particular, the present invention provides a method and compounds for producing oligopeptide thioester intermediates using Fmoc chemistry which, in turn, enables convergent synthesis strategies for chemical synthesis of polypeptides using such intermediates.

In one aspect, the present invention provides a method for preparing an oligopeptide or polypeptide product, comprising: (a) ligating in a first reaction, first and second oligopeptides each having an N-terminus and a C-terminus, wherein the first oligopeptide comprises a C-terminus having a thioester group, and an N-terminus that is substantially unreactive with the thioester group, wherein the second oligopeptide comprises an N-terminus having an unprotected cysteine, an unprotected 1,2-amino thiol, or an unprotected 1,3-amino thiol, and a C-terminus having an inactive thioester precursor, and wherein the ligating forms a first oligopeptide ligation product comprising a C-terminus having an inactive thioester precursor, and an N-terminus that is substantially unreactive with the thioester group; (b) ligating in a second reaction, third and fourth oligopeptides each having an N-terminus and a C-terminus, wherein the third oligopeptide comprises an N-terminus having a protected cysteine, a protected 1,2-amino thiol, or a protected 1,3-amino thiol, and a C-terminus comprising a thioester, wherein the fourth oligopeptide comprises an N-terminus having an unprotected cysteine, an unprotected 1,2-amino thiol, or an unprotected 1,3-amino thiol, and a C-terminus that is substantially unreactive with the unprotected cysteine, the unprotected 1,2-amino thiol, or the unprotected 1,3-amino thiol, and wherein the ligating forms a second oligopeptide ligation product comprising an N-terminus having a protected cysteine, a protected 1,2-amino thiol, or a protected 1,3-amino thiol, and a C-terminus that is substantially unreactive with the unprotected cysteine, the unprotected 1,2-amino thiol, or the unprotected 1,3-amino thiol; (c) transforming the inactive thioester precursor of the first oligopeptide ligation product of step (a) into a thioester to form a third oligopeptide ligation product having a C-terminus comprising a thioester, and an N-terminus that is substantially unreactive with the thioester group; (d) deprotecting the N-terminus of the second oligopeptide ligation product of step (b) to form a fourth ligation product comprising an N-terminus having an unprotected cysteine, an unprotected 1,2-amino thiol, or an unprotected 1,3-amino thiol, and a C-terminus that is substantially unreactive with the unprotected cysteine, the unprotected 1,2-amino thiol, or the unprotected 1,3-amino thiol; and (e) ligating the third oligopeptide ligation product of step (c) to the fourth oligopeptide ligation product of step (d) to form a fifth oligopeptide ligation product comprising an N-terminus that is substantially unreactive with an oligopeptide bearing a C-terminal thioester group, and a C-terminus that is substantially unreactive with an oligopeptide bearing an unprotected N-terminal cysteine, an unprotected 1,2-amino thiol, or an unprotected 1,3-amino thiol.

In a preferred aspect, the present invention provides a method for preparing an oligopeptide or polypeptide product further comprising the following step: (f) ligating the fifth oligopeptide ligation product of step (e) to one or more additional oligopeptides, with the proviso that the fifth oligopeptide ligation product of step (e) and the one or more additional oligopeptides bear, or are prepared to bear N-terminal and C-terminal groups capable of chemical ligation, wherein the N-terminal group capable of chemical ligation comprises an unprotected cysteine, an unprotected 1,2-amino thiol, or an unprotected 1,3-amino thiol, and wherein the C-terminal group capable of chemical ligation comprises a thioester.

In another preferred aspect, the present invention provides a method for preparing an oligopeptide or polypeptide product wherein the N-terminus of the fifth oligopeptide ligation product of step (e) comprises an unprotected N-terminal amino acid, or a protected N-terminal amino acid. In a more preferred aspect, the present invention provides a method for preparing an oligopeptide or polypeptide product wherein the protected N-terminal amino acid is cyclic. In a most preferred aspect, the present invention provides a method for preparing an oligopeptide or polypeptide product wherein the protected N-terminal amino acid comprises a protected cysteine, a protected 1,2-amino thiol, or a protected 1,3-amino thiol.

In a further preferred aspect, the present invention provides a method for preparing an oligopeptide or polypeptide product wherein the C-terminus of the fifth oligopeptide ligation product of step (e) comprises an unprotected amino acid, or an inactive thioester precursor.

In yet another preferred aspect, the present invention provides a method for preparing an oligopeptide or polypeptide product wherein any of the oligopeptides or oligopeptide ligation products having an inactive thioester precursor at the C-terminus is defined by the formula:

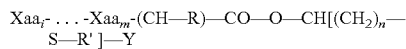

wherein $Xaa_i$ is a protected or unprotected amino acid for $i=1$ to m; m is an integer from 2 to 200; n is an integer from 1 to 10; R is an amino acid side chain; R' is a member selected from the group consisting of a sulfur protecting group and —SR"; R" is a member selected from the group consisting of $C_{2-10}$alkyl, substituted aryl having from 5 to 12 carbon atoms, substituted benzyl, and substituted heteroaryl having from 5 to 12 carbon atoms and 1 to 4 heteroatoms each independently selected from the group consisting of N, O and S; Y is an electron withdrawing group selected from the group consisting of $R^c$, $C_{1-3}$alkyl substituted with 1-3 $R^c$ groups, —C(O)—$R^d$, —S(O)$_p$—$C_{1-3}$alkyl substituted with 0-3 $R^c$ groups, and an aryl substituted with 1-3 $R^c$ groups; each $R^c$ group is independently a member selected from the group consisting of halogen, polyhaloalkyl, substituted or unsubstituted benzyl, substituted or unsubstituted aryl, —C(O)NH$_2$, —C(O)—NHNH$_2$, —S(O)$_2$NH$_2$, substituted and unsubstituted hydroxyl-amine, cyano, nitro and quaternary ammonium salts; $R^d$ is a member selected from the group consisting of hydrogen, —N($R^e$)$_2$, —OR$^e$ and —SR$^e$; each $R^e$ is independently a member selected from the group consisting of hydrogen, $C_{1-3}$alkyl substituted with 0-3 $R^c$ groups, and —SO$_2$—$C_{1-3}$alkyl substituted with 1-3 $R^c$ groups; alternatively, when two $R^e$ groups are present, they can be taken together with the atom to which they are attached to form a 5-6 membered non-aromatic heterocylic ring containing 1-3 heteroatoms each independently selected from the group consisting of N, O and S, substituted with 0-3 $R^c$ groups.

In another preferred embodiment, the present invention provides a method for preparing an oligopeptide or polypeptide product wherein R' is a sulfur protecting group.

In yet another preferred embodiment, the present invention provides a method for preparing an oligopeptide or polypeptide product wherein R' is —SR". In a further embodiment, the present invention provides a method for preparing an oligopeptide or polypeptide product wherein R" is a member selected from the group consisting of ethyl, t-butyl and substituted phenyl.

In a preferred embodiment, the present invention provides a method for preparing an oligopeptide or polypeptide product wherein the oligopeptide or polypeptide product is prepared according to the procedure in FIG. 10.

In a more preferred embodiment, the present invention provides a method for preparing an oligopeptide or polypeptide product wherein each step is performed in a solution selected from the group consisting of an organic solvent and an organic and aqueous solvent mixture.

In another preferred embodiment, the present invention provides a method for preparing an oligopeptide or polypeptide product wherein Y is —C(O)NH$_2$.

All the Y groups of the present invention are sufficiently electron-withdrawing to efficiently activate the carboxyester to allow the O to S acyl shift. Variations on the Y group, however, can have effects during ligation. For example, two peptide models of sequence LYRAF-COO—CH(CH$_2$—SH)—Y (SEQ ID NO: 1) can be synthesized: peptide A, where Y=CONH$_2$ (carboxyamide) and peptide B, where Y=COO—CH$_2$—COONH$_2$ (carboxyester). Under identical ligation conditions, peptide A generates approximately 20% of hydrolyzed carboxyester, while peptide B, where the ester moiety has a stronger electron-withdrawing effect than the carboxyamide, produces approximately 30% of hydrolyzed carboxyester. Therefore, while all the Y groups of the present invention enhance the stability of the carboxyester, some Y groups have a greater stabilizing effect on the carboxyester than other Y groups of the present invention.

A. Oligopeptide Ligation Chemistry

In the original native chemical ligation technique, e.g. as described by Dawson et al. and Kent et al., coupling of peptide fragments could take place only between an N-terminal cysteine and a C-terminal thioester. In Dawson et al. and Kent et al., a first oligopeptide is provided with an N-terminal cysteine having an unoxidized sulfhydryl side chain, and a second oligopeptide is provided with a C-terminal thioester. In the subsequent coupling reaction, the unoxidized sulfhydryl side chain of the N-terminal cysteine is condensed with the C-terminal thioester to produce an intermediate oligopeptide which links the first and second oligopeptides with a β-aminothioester bond. The β-aminothioester bond of the intermediate oligopeptide then undergoes an intramolecular rearrangement to produce the oligopeptide product that links the first and second oligopeptides via an amide bond.

A problem arises in this scheme when an oligopeptide or polypeptide is assembled from three or more fragments. In this situation, at least one fragment will have both an N-terminal cysteine and a C-terminal thioester, thereby creating the possibility for self-ligation, which under conventional reaction conditions is quite significant because of the close proximity of the reactive intra-molecular moieties. In view of this, the N-terminal cysteine of an internal fragment can be protected from such reactions by a cyclic thiazolidine protecting group, as demonstrated by Gaertner et al., Proceedings of the 17th American Peptide Symposium, pgs. 107-108 (San Diego, Jun. 9-14, 2001). These protecting group strategies, however, were previously unavailable to chemical ligations using auxiliary groups, such as disclosed by Low et al. and Botti et al.

Figure 3:
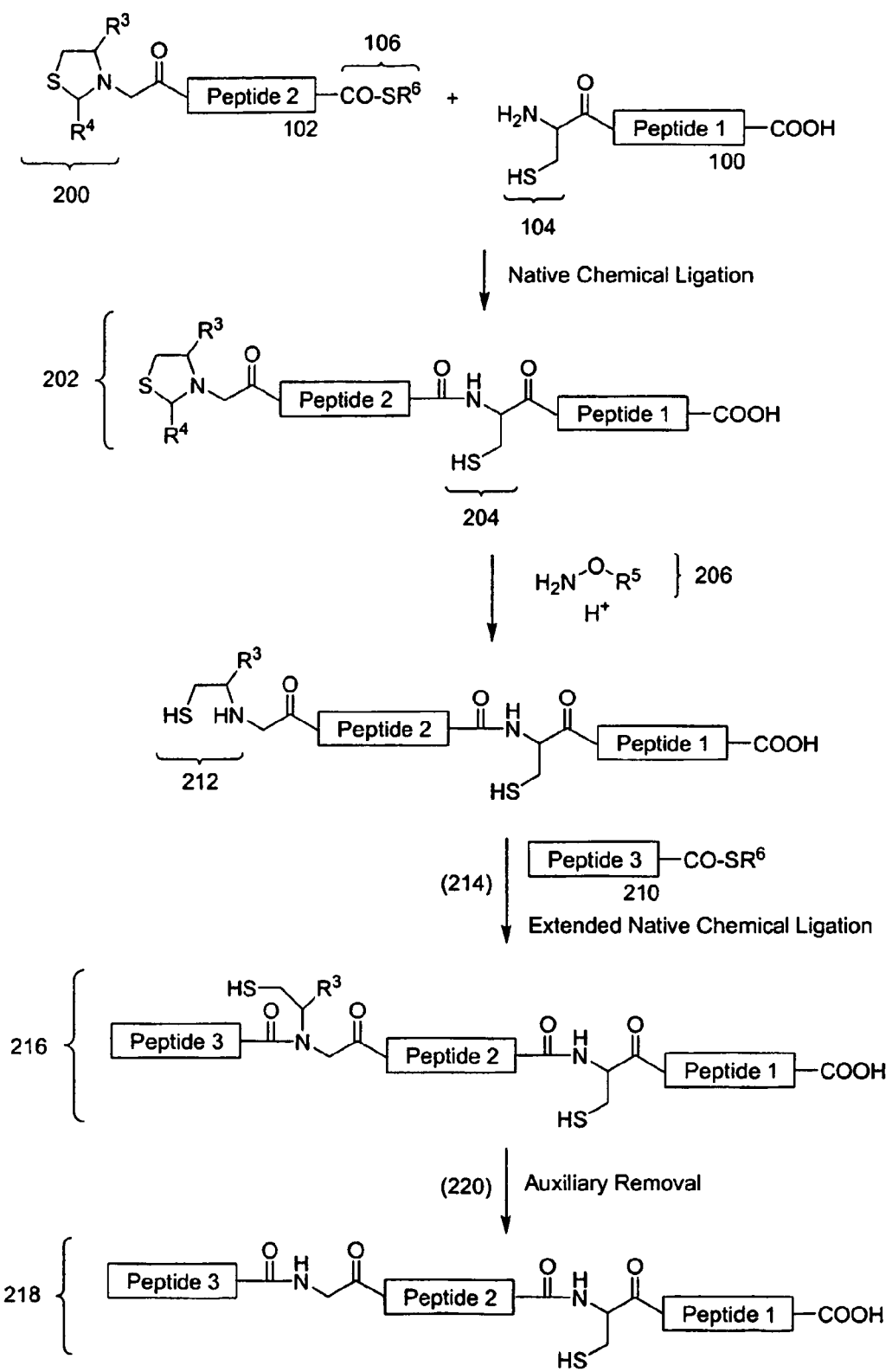
FIG. 3 illustrates native chemical ligation with the use of auxiliary groups ("extended native chemical ligation") using a heterocyclic-protected thioester-modified oligopeptide intermediate of the present invention.

In accordance with the present invention, a new class of heterocyclic protecting groups is provided that significantly increases the efficiency of ligations by preventing self-ligations in auxiliary group-assisted ligations. The operation of the heterocyclic protecting groups is illustrated in FIG. 3 for a three component ligation. In FIG. 3, radical $R^4$ is such that it promotes the opening of the thiazolidine ring, $R^5$ is hydrogen or alkyl, $R^3$ is hydrogen or an electron-donating group, and $R^6$ is an alkyl linker to an amide or an amino acid. Heterocyclic-protected thioester-modified oligopeptide (102) has thioester group (106) and exemplary heterocyclic protecting group (200). Thioester (106) reacts with N-terminal cysteine (104) of oligopeptide (100) in a procedure similar to that described by Dawson et al., Kent et al., and others (cited above) to give oligopeptide ligation product (202) consisting of oligopeptide (100) and oligopeptide (102) conjugated by amide bond (204). The oligopeptide ligation product at this step is then treated with an O-alkoxyhydroxylamine (206) under acidic conditions to open heterocyclic protecting group (200) affording a free terminal sulfhydryl group on auxiliary group (212), which is attached to the secondary amine of the N-terminal amino acid (208), which in this illustration is glycine. After such deprotection, the next thioester-modified oligopeptide (210) reacts (214) with N-terminal amine (208) in a procedure similar to that by Low et al. and Botti et al. (cited above) to provide the intermediate product (216). The auxiliary group (212) is removed (220) by acid treatment to afford the final product (218). Preferably, such removal is accomplished by treatment with HF or trifluoroacetic acid (TFA). Exemplary removal conditions include: (i) 95% HF and 5% p-cresol; (ii) TFA/bromotrimethylsilane; and (iii) 95% TFA, 2.5% triisopropylsilane (TIS), and 2.5% water. Other removal conditions will be apparent to one of skill in the art. Unless otherwise noted, these reactions and those described below take place at room temperature.

Figure 4:
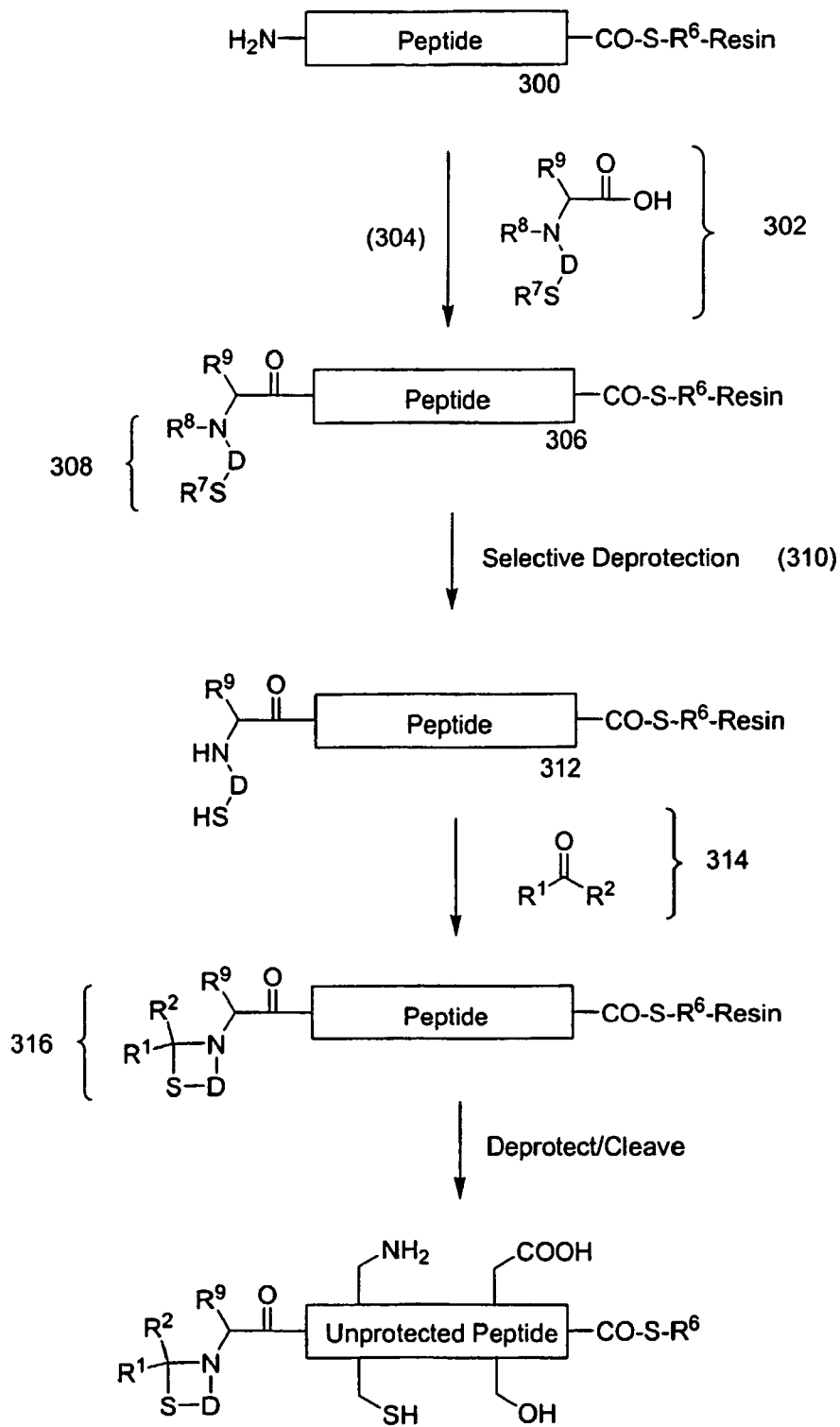
FIG. 4 illustrates a first scheme for synthesizing heterocyclic-protected thioester-modified oligopeptides of the present invention.
Figure 5:
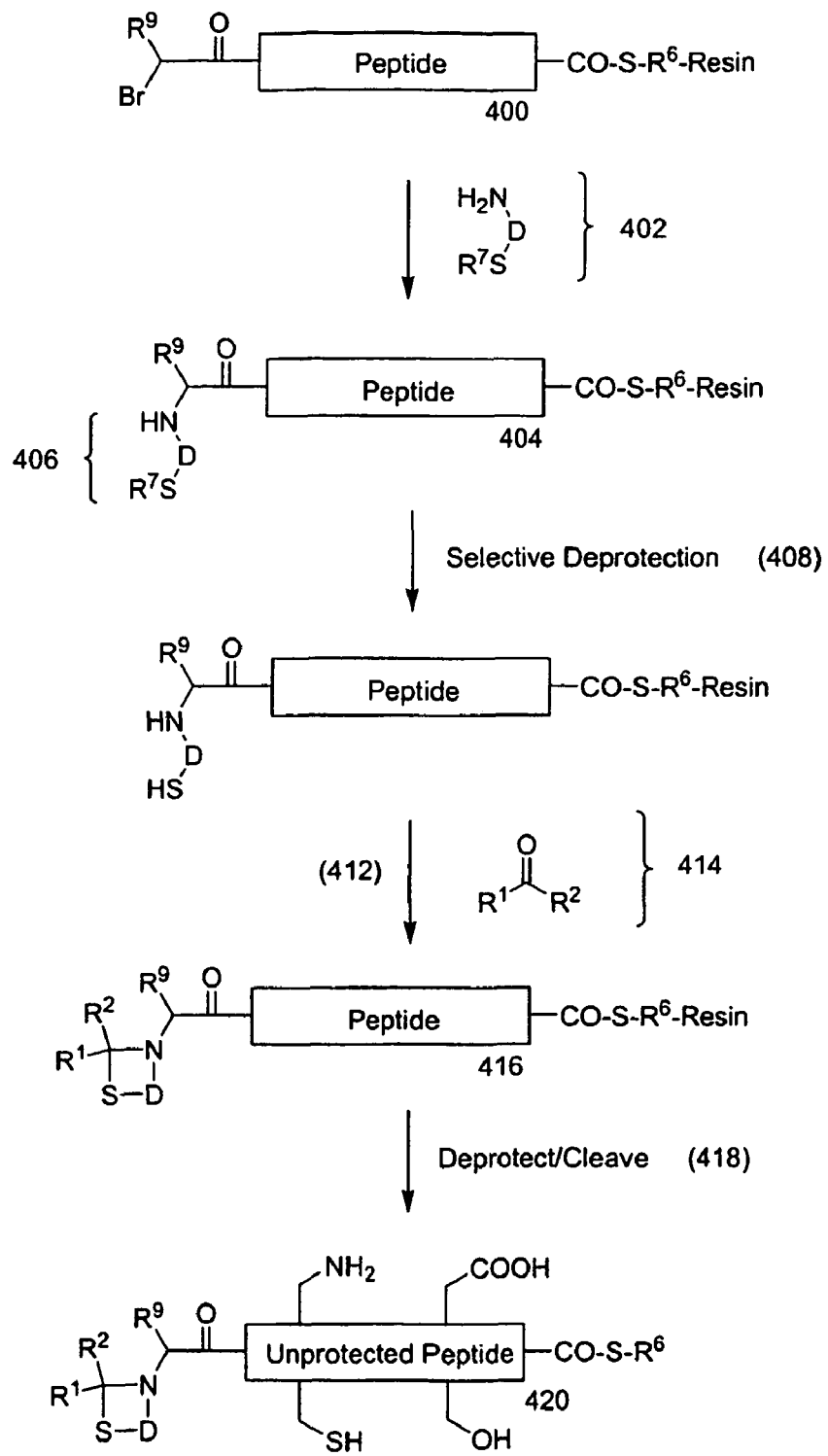
FIG. 5 illustrates a second scheme for synthesizing heterocyclic-protected thioester-modified oligopeptides of the present invention.
Figure 6:
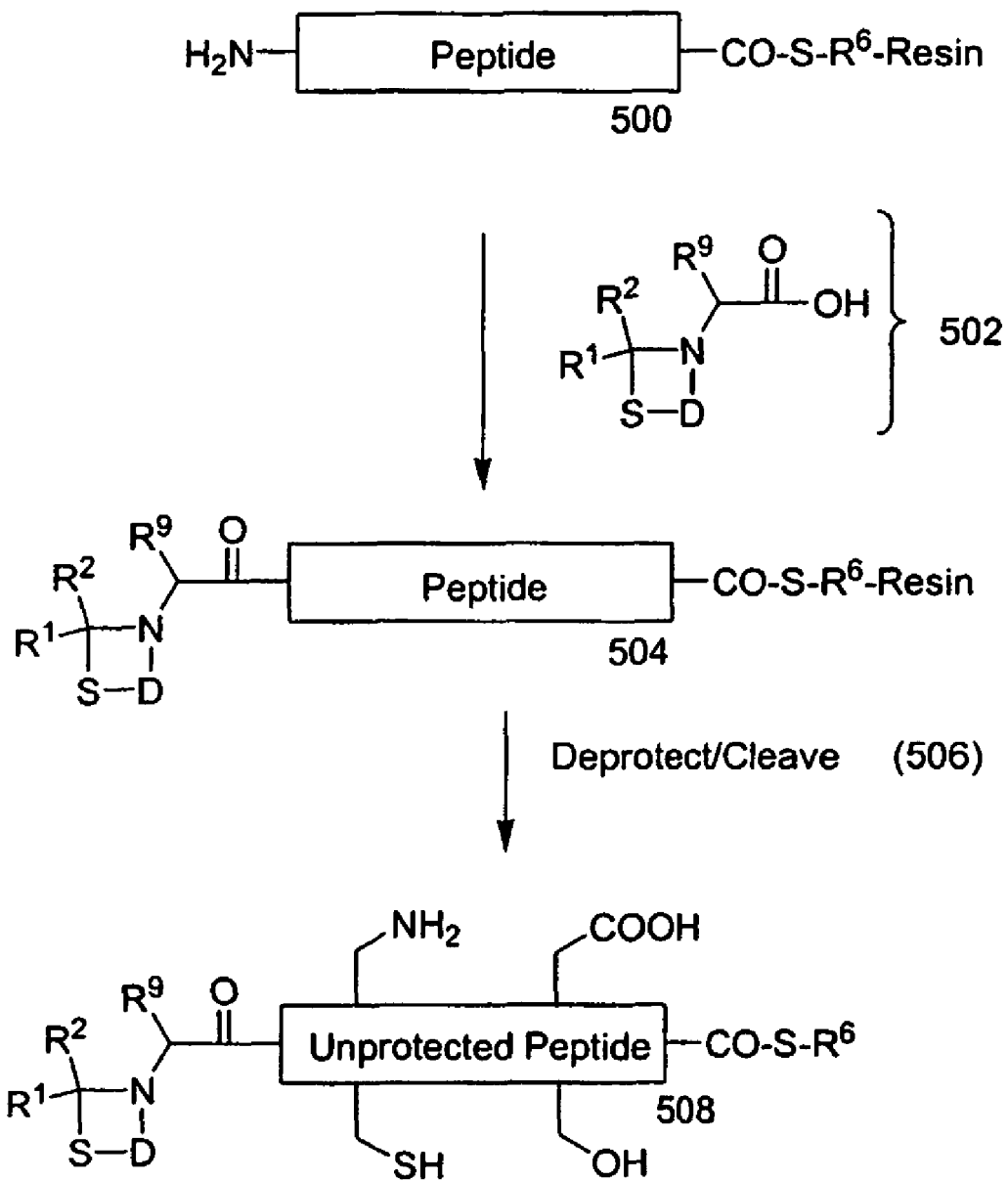
FIG. 6 illustrates a third scheme for synthesizing heterocyclic-protected thioester-modified oligopeptides of the present invention.
Figure 7:
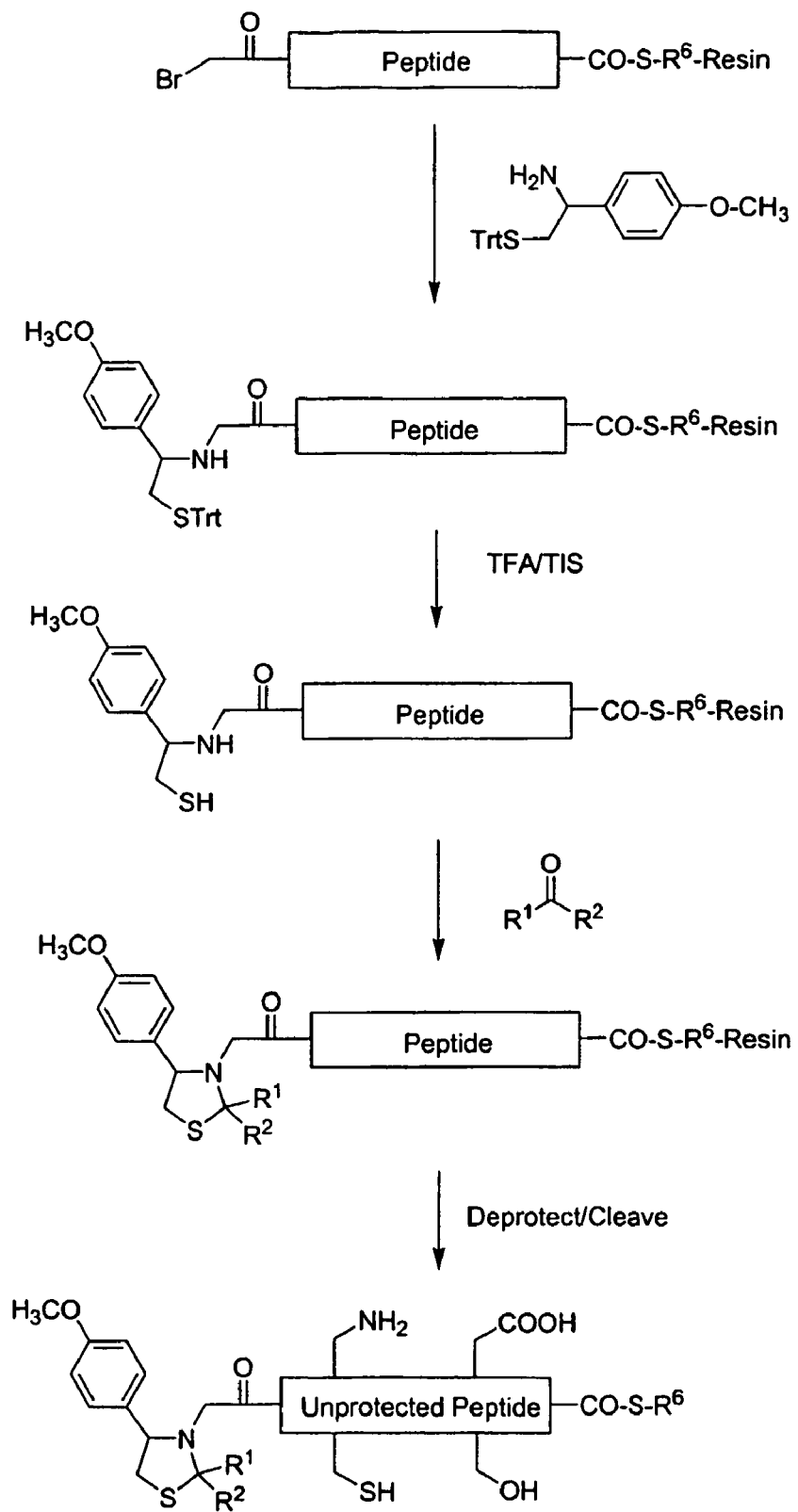
FIG. 7 illustrates a synthesis scheme for making a 4-substituted-1,3-thiazolidine-protected oligopeptide thioester.

The heterocyclic protecting group (200) can be formed at the N-terminus of an oligopeptide thioester by first synthesizing the oligopeptide thioester with an auxiliary group (212) followed by cyclization of the free sulfhydryl of the auxiliary group with the secondary α-amine (208) of the terminal amino acid. An oligopeptide thioester having an auxiliary group can be synthesized in several ways, including by halogen-mediated amino alkylation or by reductive amination. Alternatively, the heterocyclic protecting group can be formed by preparation of a fully protected amino acid monomer with the heterocyclic protecting group in place for the last addition cycle in the synthesis of a desired oligopeptide thioester. Generally, however, synthesis begins with an oligopeptide thioester attached to a resin, as shown in FIGS. 4-6.

B. Solid Phase Synthesis of Oligopeptides

The oligopeptides prepared by the methods described above, can also be prepared on a suitable solid support member. A suitable solid phase support can be selected on the basis of desired end use and suitability for various synthetic protocols. For example, in polyamide synthesis, useful solid phase support can be resins such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (Tenta-Gel™, Rapp Polymere, Tubingen, Germany), polydimethylacrylamide resin (available from Milligen/Biosearch, California), or PEGA beads (obtained from Polymer Laboratories).

Oligopeptides having a C-terminal thioester can be prepared following procedures similar to those described in the following references: Kent et al., U.S. Pat. No. 6,184,344; Tam et al., Proc. Natl. Acad. Sci., 92: 12485-12489 (1995); Blake, Int. J. Peptide Protein Res., 17: 273 (1981); Canne et al., Tetrahedron Letters, 36: 1217-1220 (1995); Hackeng et al., Proc. Natl. Acad. Sci., 94: 7845-7850 (1997); or Hackeng et al., Proc. Natl. Acad. Sci., 96: 10068-10073 (1999); Ingenito et al., J. Am. Chem, Soc., 121: 11369-11374 (1999).

Oligopeptides can be synthesized on a solid phase support typically on a 0.25 mmol scale by using the in situ neutralization/BTU activation procedure for Boc chemistry, following a procedure similar to that disclosed by Schnolzer et al., Int. J. Peptide Protein Res., 40: 180-193 (1992). (HBTU is 2-(1H-benzotriazol-1-yl)-1,1,3,3-tetramethyluronium hexafluorophosphate and Boc is tert-butoxycarbonyl). Each synthetic cycle consists of $N^\alpha$-Boc removal by a 1- to 2-minute treatment with neat TFA, a 1-minute DMF flow wash, a 10- to 20-minute coupling time with 1.0 mmol of preactivated Boc-amino acid in the presence of DIEA, and a second DMF flow wash. (TFA is trifluoroacetic acid, DMF is N,N-dimethylformamide, and DIEA is N,N-diisopropylethylamine). N-Boc-amino acids (1.1 mmol) are preactivated for 3 minutes with 1.0 mmol of HBTU (0.5 M in DMF) in the presence of excess DIEA (3 mmol). After each coupling step, yields are determined by measuring residual free amine with a conventional quantitative ninhydrin assay, e.g. as disclosed in Sarin et al., Anal. Biochem., 117: 147-157 (1981). After coupling of Gln residues, a DCM flow wash is used before and after deprotection by using TFA, to prevent possible high-temperature (TFA/DMF)-catalyzed pyrrolidone formation. Optionally, at the completion of chain assembly, a haloacetyl group, such as bromoacetyl, can be added, in a procedure similar to that disclosed by Zuckerman et al., J. Am. Chem. Soc. 114: 10646-10647 (1992), as one route for synthesizing compounds of the present invention.

Oligopeptide thioesters of the present invention can be synthesized using either Fmoc or Boc chemistries. When Fmoc chemistry is employed, a 3-carboxypropanesulfonamide "safety catch" linker is used to generate the thioester. Thioester oligopeptides described above are preferably synthesized on a trityl-associated mercaptopropionic acid-leucine (TAMPAL) resin, made in a procedure similar to that disclosed by Hackeng et al. (1999), or comparable protocol. $N^\alpha$-Boc-Leu (4 mmol) is activated with 3.6 mmol of HBTU in the presence of 6 mmol of DIEA and coupled for 16 minutes to 2 mmol of p-methylbenzhydrylamine (MBHA) resin, or the equivalent. Next, 3 mmol of S-trityl mercaptopropionic acid is activated with 2.7 mmol of HBTU in the presence of 6 mmol of DIEA and coupled for 16 minutes to Leu-MBHA resin. The resulting TAMPAL resin can be used as a starting resin for polypeptide-chain assembly after removal of the trityl protecting group with two 1-minute treatments with 3.5% triisopropylsilane and 2.5% $H_2O$ in TFA. The thioester bond can be formed with any desired amino acid by using standard in situ-neutralization peptide coupling protocols for 1 hour, in a procedure similar to that disclosed in Schnolzer et al. (cited above). Treatment of the final oligopeptide with anhydrous HF yields the C-terminal activated mercaptopropionic acid-leucine (MPAL) thioester oligopeptides.

In a preferred embodiment, oligopeptide thioesters are deprotected and cleaved from the resin by treatment with anhydrous HF for 1 hour at 0° C. with 4% p-cresol as a scavenger. The imidazole side-chain 2,4-dinitrophenyl (DNP) protecting groups remain on the His residues because the DNP-removal procedure is incompatible with C-terminal thioester groups. However, DNP is gradually removed by thiols during the ligation reaction. After cleavage, oligopeptide thioesters can be precipitated in ice-cold diethylether, dissolved in aqueous acetonitrile, and lyophilized.

C. Preparation of Heterocyclic Protected Oligopeptide Thioester Intermediates

Reaction of N-Terminal Amines with Protected Amino Acids

Heterocyclic protected oligopeptide thioesters are synthesized by a variety of schemes, as illustrated in FIGS. 4-6. In Scheme 1, shown in FIG. 4, a free N-terminal amine of oligopeptide thioester (300) is reacted with protected amino acid (302), having auxiliary group (-D-S—$R^7$), in a standard coupling reaction (304), e.g. Schnolzer et al. (cited above), to afford oligopeptide thioester (306) having auxiliary group (308) attached to the α-amine. $R^9$ is amino acid side chain, other than the side chain for proline. Preferably, $R^9$ is a non-sterically hindering amino acid side chain, or the side chain of histidine. More preferably, $R^9$ is hydrogen, methyl, hydroxymethyl, or the side chain of histidine. Oligopeptide thioester (312) is formed by selective deprotection (310) of the α-amine and the sulfhydryl group of the auxiliary group. In a preferred embodiment, selective deprotection (310) is achieved by mild acid treatment, for example, trifluoroacetic acid (TFA) under conventional reaction conditions, e.g. Green and Wuts (cited below), in the presence of a scavenger, such as triisopropylsilane (TIS), whenever $R^8$ is Boc, or like protecting group, and $R^7$ is triphenylmethyl, i.e. trityl, or like protecting group. Guidance for selecting appropriate amino and sulfhydryl protecting groups and $N^\alpha$ protecting groups for selective deprotection is found in Greene and Wuts, Protecting Groups in Organic Chemistry, 3rd Edition (John Wiley & Sons, New York, 1999). Following deprotection, the oligopeptide thioester (312) is reacted with substituted carbonyl (314) so that heterocyclic protecting group (316) is formed.

Exemplary $R^8$ protecting groups include t-butylcarbamate (Boc), 9-fluorenylmethylcarbamate (Fmoc), 4-nitrophenylethylsulfonyl-ethyloxycarbonyl (NSC), 2,2,2-trichloroethylcarbamate (Troc), bromobenzylcarbamate (BrZ), chlorobenzylcarbamate (ClZ), and the like. In a preferred embodiment, $R^8$ protecting groups are Boc and Fmoc.

Exemplary $R^7$ protecting groups include benzyl, 4-methylbenzyl, 4-methoxybenzyl, trityl, acetamidomethyl, trimethylacetamidomethyl, xanthyl, and the like. Further protecting groups useful in the present invention will be apparent to one of skill in the art.

In regard to the other substituents of the Figures, $R^1$ and $R^2$ are selected to promote the opening of the heterocyclic protecting group under acidic conditions in the presence of a nucleophilic agent. In a preferred embodiment, $R^1$ and $R^2$ are separately hydrogen, electron withdrawing-substituted alkyl having from 1 to 3 carbon atoms, alkylcarbonyl having 2 to 3 carbon atoms, or arylcarbonyl having 7 to 10 carbon atoms.

D is a linking moiety that together with a free sulfhydryl ("HS-D-") is referred to herein as an auxiliary group. In one aspect, D is an alkyl, alkenyl, aryl, aralkyl, cycloalkyl moiety having from 2 to 16 carbon atoms and from 0 to 4 heteroatoms that: (i) maintains the heterocyclic sulfur closely adjacent to the heterocylic nitrogen after deprotection in order to promote the rearrangement reaction of native chemical ligation; and (ii) provides a cleavable bond to the heterocyclic nitrogen so that after deprotection and fragment coupling, the auxiliary group is removed. In a preferred embodiment, whenever in the form "HS-D," D maintains the sulfhydryl group within an equivalent distance of 2 to 3 carbon-carbon bond lengths to the $N^\alpha$ of the N-terminal amino acid of the oligopeptide thioester reactant, the carbon-carbon bonds being those of a linear alkyl group. In a preferred aspect, the auxiliary group is an ethylthiol.

$R^3$ taken alone is hydrogen or an electron donating group having from 1 to 12 carbon atoms and from 0 to 4 heteroatoms selected from the group consisting of nitrogen, oxygen, sulfur, and phosphorus. Preferably, $R^3$ taken alone is hydrogen or electron donating group having from 1 to 8 carbon atoms and from 0 to 2 heteroatoms selected from the group consisting of nitrogen, oxygen, and sulfur. Still more preferred, $R^3$ taken alone is hydrogen, phenyl, electron donating-substituted phenyl, 2- or 4-picolyl, or electron donating-substituted 2- or 4-picolyl. Still more preferably, $R^3$ taken alone is hydrogen or methoxy-substituted phenyl. Most preferably, $R^3$ taken alone is 4-methoxyphenyl or 2,4-dimethoxyphenyl.

$R^6$ is alkyl having from 1 to 6 carbon atoms or alkylaryl having from 6 to 8 carbon atoms, —$CH_2$—$CONH_2$, —$CH_2CH_2CONH_2$, or —$(CH_2)_k$—CO-Xaa, wherein subscript k is an integer equal to 1 or 2 and Xaa is an amino acid.

$R^9$ is an amino acid side chain, other than those of proline and cysteine. More preferably, $R^9$ is an amino acid side chain other than those of proline, cysteine, valine, isoleucine, and threonine. In further preference, $R^9$ is hydrogen, methyl, hydroxymethyl, or the side chain of histidine. Most preferably, $R^9$ is hydrogen or methyl.

Reaction of Bromoacetylated Oligopeptides with Auxiliary Group Precursors

A second scheme (Scheme 2) for synthesizing heterocyclic protected oligopeptide thioesters is shown in FIG. 5. This Scheme roughly follows the procedure disclosed by Botti et al. (cited above). Bromoacetylated oligopeptide thioester (400) is reacted with S-protected ethylamine or S-protected aminothiophenyl (402), or like group, to afford oligopeptide thioester (404) with auxiliary group (406), after which the sulfhydryl protecting group ($R^7$) is removed (408) with mild acid. In the case of $R^7$ being a trityl group, $R^7$ is removed with TFA in the presence of a trityl scavenger, such as TIS. The α-amine of oligopeptide thioester (410) and the free sulfhydryl of the auxiliary group are reacted (412) with carbonyl (414) to form a heterocyclic protected oligopeptide thioester (416). Preferably, carbonyl (414) is formaldehyde, acetaldehyde, acetone, or the like. More preferably, $R^1=R^2$ so that chiral forms are not produced. In some embodiments, it can be desirable to employ either or both $R^1$ and $R^2$ as an affinity or chromatography purification aid. For example, $R^1$ or $R^2$ can be biotin, digoxigenin, or like affinity group, connected to a linking moiety, e.g. biotin-$(CH_2)_n$—, or $R^1$ or $R^2$ can be a hydrophobic or hydrophilic group designed to modify chromatographic retention time to aid in purification. Heterocyclic protected oligopeptide thioester (416) is then deprotected and cleaved from the resin (418), e.g. by HF treatment, to give final product (420).

Reaction of N-Terminal Amines with Auxiliary Group Derivatized Amino Acids

In a third Scheme (Scheme 3) shown in FIG. 6, the heterocyclic protecting group is added to the oligopeptide thioester by coupling a derivatized amino acid already having the group in place. Oligopeptide thioester (500) having a free N-terminal amine is reacted with a derivatized amino acid (502) in a conventional solid phase peptide synthesis reaction to afford oligopeptide (504), after which it is deprotected and cleaved (506) from the synthesis column to afford the final product (508). Derivatized amino acid (502) can be prepared by several routes. In a preferred embodiment, derivatized amino acid (502) is prepared by first synthesizing an intermediate having an auxiliary group-substituted $N^\alpha$ in the following nucleophilic substitution reaction:

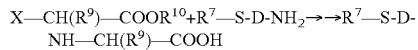

where X is halogen, preferably bromo, and $R^{10}$ is a conventional protecting group or a solid phase support. The sulfhydryl group of the resulting $N^\alpha$-substituted amino acid can be afforded by conventional protocols (e.g. TFA/TIS for tritylprotected sulfhydryl), after which it can be reacted with a substituted formaldehyde, $CO(R^1)(R^2)$, and the $N^\alpha$ amine to provide the derivatized amino acid (502). Alternatively, the above intermediate can be prepared via nucleophilic substitution or by reductive amination, as shown in the following reaction scheme:

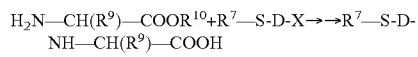

wherein X is a halogen for the nucleophilic substitution route, and X is a carbonyl for the synthesis via reductive amination. One of skill in the art will appreciate that when the product above is prepared via reductive amination (when X is a carbonyl), radical D of the product is chain extended by a single carbon atom. Accordingly, radical D in the starting material of the scheme above is a methylene or ethylene unit in some embodiments, and a direct bond in other embodiments.

In a preferred embodiment, heterocyclic-protected oligopeptide thioester intermediates are used in native chemical ligation under conditions similar to those described by Hackeng et al. (1999), or like conditions. 0.1 M phosphate buffer (pH 8.5) containing 6 M guanidine, 2% (vol/vol) benzylmercaptan, and 2% (vol/vol) thiophenol is added to dry peptides to be ligated, affording a final peptide concentration of 1-3 mM at about pH 7. In a preferred embodiment, the ligation reaction can be performed in a heating chamber at 37° C. under continuous stirring and can be periodically vortexed to equilibrate the thiol additives. The reaction can be monitored for degree of completion by MALDI-MS or HPLC and electrospray ionization MS.

Deprotection of N-Terminal Amines and Removal of Auxiliary Groups

After a native chemical ligation reaction is completed or stopped, the N-terminal heterocyclic ring of the product can be opened by treatment with a deprotecting agent that is nucleophilic under acidic conditions. Such agents include certain O-alkylhydroxylamines, hydrazines, and like reagents. More preferably, the N-terminal heterocyclic ring of the product is opened by treatment with O-methylhydroxylamine (0.5 M) at pH 3.5-4.5 for 2 hours at 37° C., after which a 10-fold excess of Tris-(2-carboxyethyl)-phosphine (TCEP) is added to the reaction mixture to completely reduce any oxidizing reaction constituents prior to purification of the product. Preparative HPLC is the preferred method of purification. Preferably, fractions containing the ligation product are identified by electrospray MS, pooled, and lyophilized. Other reducing agents that can be used in place of Tris-(2-carboxyethyl)-phosphine include β-mercaptoethanolamine, dithiotreitol, and the like.

Returning to the deprotection strategies, N-terminal thiazolidines can be ring-opened with a variety of nucleophilic agents under acidic conditions, as discussed above. Ring-opening under acidic conditions is dependent on the C2 substituents (Wohr et al., J. Am. Chem. Soc., 118: 9218 (1994)). The following agents can be used as thiazolidine ring-opening agents: O-methylhydroxylamine and other hydroxylamine derivatives. Hydrazine or any of its derivatives, as well as thiosemicarbazides, which are nucleophilic under acidic conditions, can also be used, but this family of reagents is generally more toxic than the former, and the condensation product (hydrazone, thiosemicarbazone, respectively) is less stable than the oxime. Preferably, Tris-(2-carboxyethyl)-phosphine (TCEP), or like reducing agent, is used in the deprotection reaction to rapidly and stoichiometrically reduce most peptides and sulfhydryls even under acidic conditions (Burns et al., J. Org. Chem., 56: 2648-2650, 1991). Preferably, O-methoxyhydroxylamine is used as the thiazolidine ring-opening agent. O-methoxyhydroxylamine reacts with the masked aldehyde function in the thiazolidine ring to form an oxime, as shown below:

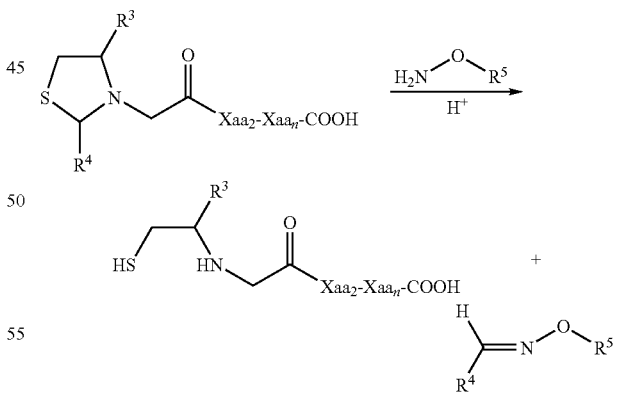

wherein $R^3$ is as defined above, and $R^4$ and $R^5$ can be, for example, hydrogen, alkyl, amide, ester, halogen, cycloalkyl, heterocyclyl, aryl and heteroaryl, all optionally substituted. In a preferred embodiment, $R^4$ promotes the deprotection of the thiazolidine ring. Such substituents will be apparent to one of skill in the art. One of skill in the art will appreciate that other agents can also be used to deprotect thiazolidine protecting groups of the present invention.

Auxiliary groups can be removed after each ligation step, or they can be removed all at the same time after the polypeptide final product is completely synthesized. Depending on the structure of the linking moiety "D" a variety of removal procedures are available. In the preferred form of D that donates electrons to the $N^\alpha$ of the adjacent amino acid, removal of the auxiliary group can be readily effected by acidic conditions, such as used in conventional peptide synthesis for side chain deprotection. Exemplary acids for such cleavage include HF, TFA, trifluoromethanesulfonic acid (TFMSA), and the like. In some embodiments, conventional scavenging agents, e.g. 5% p-cresol, or the like, can be used to bind or react with aryl, thiol, or other reactive moieties, and to prevent undesired secondary reactions with amino acid side chains.

After the synthesis is completed and the final product purified, the final polypeptide product can be refolded by conventional techniques similar to those described by Creighton, Meth. Enzymol., 107: 305-329 (1984); White, Meth. Enzymol., 11: 481-484 (1967); Wetlaufer, Meth. Enzymol., 107: 301-304 (1984); Misawa et al., Biopolymers, 51: 297-307 (1999); Anfinsen, Science, 181: 223-230 (1973); and the like. Preferably, a final product is refolded by air oxidation by dissolving the reduced lyophilized product (at about 0.1 mg/mL) in 1 M guanidine hydrochloride (or like chaotropic agent) with 100 mM Tris, 10 mM methionine, at pH 8.6. After gentle overnight stirring, the re-folded product is isolated by reverse phase HPLC with conventional protocols.

D. Preparation of Disulfide-Protected Carboxythioester Groups

S-Disulfide-protected 2-mercapto carboxyester of an oligopeptide intermediate can be prepared by a variety of possibilities including the following schemes (FIG. 10 A, B, C, D): A) Formation of 2 S-Disulfide-protected mercapto carboxyester from a S-protected 2-mercapto carboxyester peptide resin whose thiol is protected with a mildly or super acid-labile protecting group followed by deprotection of the thiol prior to cleavage from the synthesis resin and formation of a disulfide prior or concomitantly to the cleavage. B) addition of a 2-S-Disulfide-protected, 1-Hydroxy-1-carboxy ethane (alternatively called 3-S-Disulfide-protected, 2-Hydroxy-propanoic acid) to the resin, and then after attachment of the first amino acid of choice through an ester linkage, a standard Fmoc solid phase peptide synthesis yields the desired peptide. First, a protected thiol precursor, PG-S—$(CH_2)_n$—CH(OH)COOH, is coupled using carbodiimide chemistry (DCC, or DIC preferably) with a mild activated agent like trichlorophenol or N-hydroxysuccinimide to an amino-derivatized synthesis resin. The resin can then be functionalized with the first amino acid of the sequence using a base-catalyzed coupling like HBTU/DIEA with DMAP. C) Coupling of a disulfide protected carboxyester of the first amino acid monomer to the resin. Preferably, disulfide protected carboxythioesters are formed prior to cleavage of the intermediate from the synthesis resin. And D), directly from the S-protected cysteine derivative of choice (disulfide protected and non) by treatment with $NaNO_2$ in acidic medium or by analogue transformation of a nitrogen into a OH group.

More generally, a protected thiol precursor, PG-S—$(CH_2)_n$—CH(OCO-$Xaa_1$-Fmoc)COOH, is coupled using conventional chemistry to an amino-derivatized synthesis resin:

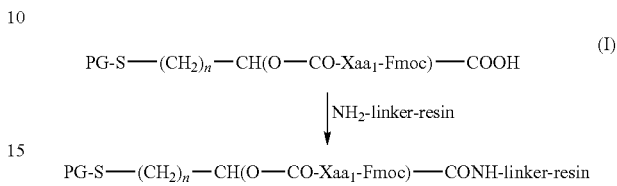

After the final amino acid is coupled, the Fmoc is removed, followed by removal of the protecting group, PG, with mild acid. Then, formation of a peptide S-Disulfide-protected 2-mercapto carboxyester can be accomplished according to FIG. 10A. Preferably, PG is monomethoxytrityl, and is removed by conventional conditions, e.g. 1-2% trifluoroacetic acid and TIS. Removal of PG gives the compound below, which is then treated with a disulfide-forming reagent to give the final disulfide protected carboxythioester. Disulfide-forming reagents include symmetric disulfides such as symmetric aromatic disulfides, symmetric hindered alkyl disulfides, and the like. More particularly, disulfide-forming reagents include bithiobis(pyridine), dithiobis(5-nitropyridine), dithiobis-t-butyl, R"—SO—S—R", and the like.

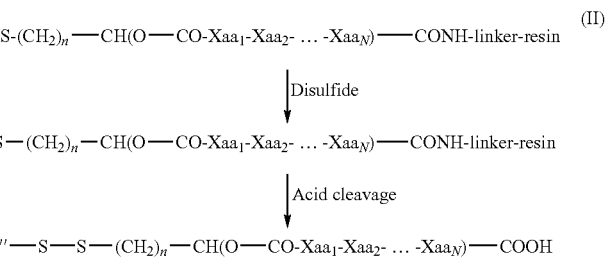

Alternatively, PG may be picolyl, ACM, Phenacyl, or other acid stable protecting groups known to one of skill in the art.

The initial precursor (I) is produced as follows. Chloroalanine is treated with sodium nitrate or potassium nitrate under acidic conditions to convert the α-amine to a hydroxyl, as shown:

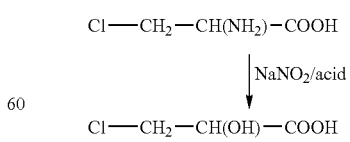

The chloro is then replaced with a protected sulfur or a protected disulfide, e.g. via nucleophilic displacement. Preferably, the chloro is replaced with a mercapto generating labile sulfur protecting group like 4-methoxytrityl mercaptan, after which the product is reacted with an Fmoc-protected activated amino acid like Fmoc-AA-OPFP or Fmoc-AA-OSu to give compound (I).

After compound (II) is used in a ligation reaction, a free thioester is generated by treating the ligation product with a reducing agent, preferably a thiol reducing agent, such as benzenethiol. The reducing agent frees the thiol group which spontaneously forms a thioester.

IV. Oligopeptides, Polypeptides and Proteins

In another aspect, the present invention provides a compound of the formula:

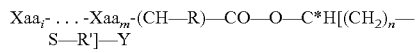

wherein $Xaa_i$ is a protected or unprotected amino acid for $i=1$ to m; m is an integer from 2 to 200; n is an integer from 1 to 10; C* is a chiral carbon in either the R or the S configuration, and substantially free of the other configuration; R is an amino acid side chain; R' is a member selected from the group consisting of a sulfur protecting group, —SR" and hydrogen; R" is a member selected from the group consisting of $C_{2-10}$alkyl, substituted aryl having from 5 to 12 carbon atoms, substituted benzyl, and substituted heteroaryl having from 5 to 12 carbon atoms and 1 to 4 heteroatoms each independently selected from the group consisting of N, O and S; Y is an electron withdrawing group consisting of $R^c$, $C_{1-3}$alkyl substituted with 1-3 $R^c$ groups, —C(O)—$R^d$, —S(O)$_p$—$C_{1-3}$alkyl substituted with 0-3 $R^c$ groups, and an aryl substituted with 1-3 $R^c$ groups; each $R^c$ group is independently a member selected from the group consisting of halogen, polyhaloalkyl, substituted or unsubstituted benzyl, substituted or unsubstituted aryl, —C(O)NH$_2$, —C(O)—NHNH$_2$, —S(O)$_2$NH$_2$, substituted and unsubstituted hydroxyl-amine, cyano, nitro and quaternary ammonium salts; p is an integer from 1 to 2; $R^d$ is a member selected from the group consisting of hydrogen, —N($R^e$)$_2$, —O$R^e$ and —S$R^e$; each $R^e$ is independently a member selected from the group consisting of hydrogen, $C_{1-3}$alkyl substituted with 0-3 $R^c$ groups, and —SO$_2$—$C_{1-3}$alkyl substituted with 1-3 $R^c$ groups; alternatively, when two $R^e$ groups are present, they can be taken together with the atom to which they are attached to form a 5-6 membered non-aromatic heterocylic ring containing 1-3 heteroatoms each independently selected from the group consisting of N, O and S, substituted with 0-3 $R^c$ groups.

In another preferred embodiment, the present invention provides a compound wherein R' is a sulfur protecting group.

In yet another preferred embodiment, the present invention provides a compound wherein R' is —SR". In yet still another preferred embodiment, the present invention provides a compound wherein R' is hydrogen. In a further embodiment, the present invention provides a compound wherein R" is a member selected from the group consisting of ethyl, t-butyl and substituted phenyl.

In another preferred embodiment, the present invention provides a compound wherein Y is —C(O)NH$_2$.

In yet another aspect, the present invention provides a compound of the formula:

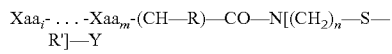

wherein $Xaa_i$ is a protected or unprotected amino acid for $i=1$ to m; m is an integer from 2 to 200; n is an integer from 1 to 10; R is an amino acid side chain; R' is a sulfur protecting group; Y is an electron withdrawing group selected from the group consisting of $R^c$, $C_{1-3}$alkyl substituted with 1-3 $R^c$ groups, —C(O)—$R^d$, —S(O)$_p$—$C_{1-3}$alkyl substituted with 0-3 $R^c$ groups, and an aryl substituted with 1-3 $R^c$ groups; each $R^c$ group is independently a member selected from the group consisting of halogen, polyhaloalkyl, substituted or unsubstituted benzyl, substituted or unsubstituted aryl, —C(O)NH$_2$, —C(O)—NHNH$_2$, —S(O)$_2$NH$_2$, substituted and unsubstituted hydroxyl-amine, cyano, nitro and quaternary ammonium salts; p is an integer from 1 to 2; $R^d$ is a member selected from the group consisting of hydrogen, —N($R^e$)$_2$, —O$R^e$ and —S$R^e$; each $R^e$ is independently a member selected from the group consisting of hydrogen, $C_{1-3}$alkyl substituted with 0-3 $R^c$ groups, —SO$_2$—$C_{1-3}$alkyl substituted with 1-3 $R^c$ groups; alternatively, when two $R^e$ groups are present, they can be taken together with the atom to which they are attached to form a 5-6 membered non-aromatic heterocylic ring containing 1-3 heteroatoms each independently selected from the group consisting of N, O and S, substituted with 0-3 $R^c$ groups.

In a further aspect, the present invention provides a compound of the formula:

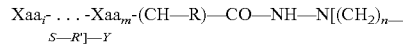

wherein $Xaa_i$ is a protected or unprotected amino acid for $i=1$ to m; m is an integer from 2 to 200; n is an integer from 1 to 10; R is an amino acid side chain; R' is a sulfur protecting group; Y is an electron withdrawing group selected from the group consisting of $R^c$, $C_{1-3}$alkyl substituted with 1-3 $R^c$ groups, —C(O)—$R^d$, —S(O)$_p$—$C_{1-3}$ alkyl substituted with 0-3 $R^c$ groups, and an aryl substituted with 1-3 $R^c$ groups; each $R^c$ group is independently a member selected from the group consisting of halogen, polyhaloalkyl, substituted or unsubstituted benzyl, substituted or unsubstituted aryl, —C(O)NH$_2$, —C(O)—NHNH$_2$, —S(O)$_2$NH$_2$, substituted and unsubstituted hydroxyl-amine, cyano, nitro and quaternary ammonium salts; p is an integer from 1 to 2; $R^d$ is a member selected from the group consisting of hydrogen, —N($R^e$)$_2$, —O$R^e$ and —S$R^e$; each $R^e$ is independently a member selected from the group consisting of hydrogen, $C_{1-3}$alkyl substituted with 0-3 $R^c$ groups, —SO$_2$-$C_{1-3}$ alkyl substituted with 1-3 $R^c$ groups; alternatively, when two $R^e$ groups are present, they can be taken together with the atom to which they are attached to form a 5-6 membered non-aromatic heterocylic ring containing 1-3 heteroatoms each independently selected from the group consisting of N, O and S, substituted with 0-3 $R^c$ groups.

V. EXAMPLES

Example 1

Preparation of LYRAF-O—COCH(CH$_2$—S—S-Pyr) CONH$_2$ (SEQ ID NO: 1) (FIG. 10A)

Rink amide resin (Novabiochem 0.61 mmol/g, 0.1 mmol) was swollen in DMF. After Fmoc removal with a solution 20% of Piperidine in DMF, MmtSCH$_2$CH(OH)COOH (0.5 mmol) was activated with N-hydroxysuccinimide (1.2 eq) and Diisopropylcarbodiimide (1.2 eq.) and coupled to the resin overnight.

A sample of the resin gave negative ninhydrin reaction. Capping with BocGlyOSu.

The first Fmoc amino acid (1 mmol) was activated with HBTU/DIEA in the presence of a catalytic amount of DMAP and it was coupled to the resin for 1 hour. A double coupling was necessary. Then the SPPS was performed manually, using 10 excess of each activated Fmoc amino acid and monitored with the ninhydrin test.

After the final cycle the Fmoc was cleaved and the peptide-resin was washed successively with DMF, DCM, DCM and MeOH and it was dried.

It was then suspended in a mixture TFA/TIS/H$_2$O: 95/2.5/2.5 containing 5 equivalents of 2.2'-dithio-bis-(pyridine)* (0.5 mmol, 110.2 mg) under stirring at room temperature After 2 h 45 the resin was removed by filtration and washed with TFA. Diethyl ether was added and the solid was collected by filtration, washed with diethyl ether and dried in vacuo.

Example 2

Preparation of Chlorolactic Acid—from Beta-Chloroalanine to Chlorolactic Acid (FIGS. 10B, 10C)

Following a procedure similar that described in Morin et al. *Synthesis* (1987), 479-480, beta-Chloroalanine (MW=160, 1 g, 6.25 mmol) was dissolved in 20 ml of 1 N aqueous sulfuric acid and the solution was stirred at 4° C. A freshly prepared solution of sodium nitrite (MW=69, 1.36 g, 19.75 mmol) in water (21 ml) was slowly added, dropwise, over 45 minutes, the temperature being maintained at 4° C. After the addition the mixture was left stirring 1 h at 4° C. then, overnight at room temperature.

Solid sodium hydrogen carbonate was added in order to bring the pH above 2. The solution was then saturated with sodium chloride and extracted with ethyl acetate (6×40 ml) maintaining the pH between 2 and 3 with 1N sulfuric acid. After drying with sodium sulfate the organic phase was evaporated to afford a pale yellow solid. It was washed with hexane and filtered. 550 mg of white crystals were isolated.

Example 3

Preparation of S-Mmt Lactic Acid (3S-4'Methoxytrityl-2-hydroxy-propanoic Acid) by Reaction of Chlorolactic Acid with Mmt-SH (FIGS. 10b, 10c)

Following a procedure similar to Hope et al. J. Chem. Soc. (C) (1979), 2475-2478), a solution of Chlorolactic acid (MW=125, 1.5 g, 12 mmol) and sodium hydroxide (480 mg, 12 mmol) in hot ethanol (10 ml, 50° C.) was added to a stirred solution of 4-Methoxymethyl mercaptan (MW=306.4, 3.68 g, 12 mmol) and sodium hydroxide (480 mg, 12 mmol) in hot ethanol (10 ml, 50° C.). The volume was brought up to 60 ml with ethanol. The mixture was heated under reflux for 8 hours, then it was left stirring at room temperature overnight. The solvent was evaporated, the solid residue was dissolved in water and the pH was brought to =4. The mixture was extracted with ethyl acetate (4×50 ml). The combined organic extracts were dried over magnesium sulfate and the solvent was removed under reduced pressure to give 4.52 g of an orange oil which solidified at room temperature. 2.5 g of the crude material was washed with hexane, filtered and dried. 1.4 g of a yellow solid foam was recovered.

Example 4

MmtSCH$_2$CH(OH)COOH+FmocPheOPfp

To a stirred solution of MmtSCH$_2$CH(OH)COOH (MW=394, 100 mg, 0.25 mmol) and FmocPheOPfp (MW=553.5, 144 mg, 0.26 mmol) in DMF (1 ml) was added dropwise DIEA (0.75 mmol, 131 µl). After 2 hours at room temperature the reaction was completed as confirmed by HPLC analysis.

Water was added to the reaction mixture and the pH was brought to 3.5/4 with KHSO$_4$. The mixture was extracted with ethyl acetate. The combined organic extracts were dried over magnesium sulfate and the solvent was removed under reduced pressure to give 250 mg of crude product. After purification by HPLC, 80 mg of pure product was recovered.

Example 5

Figure 10D:
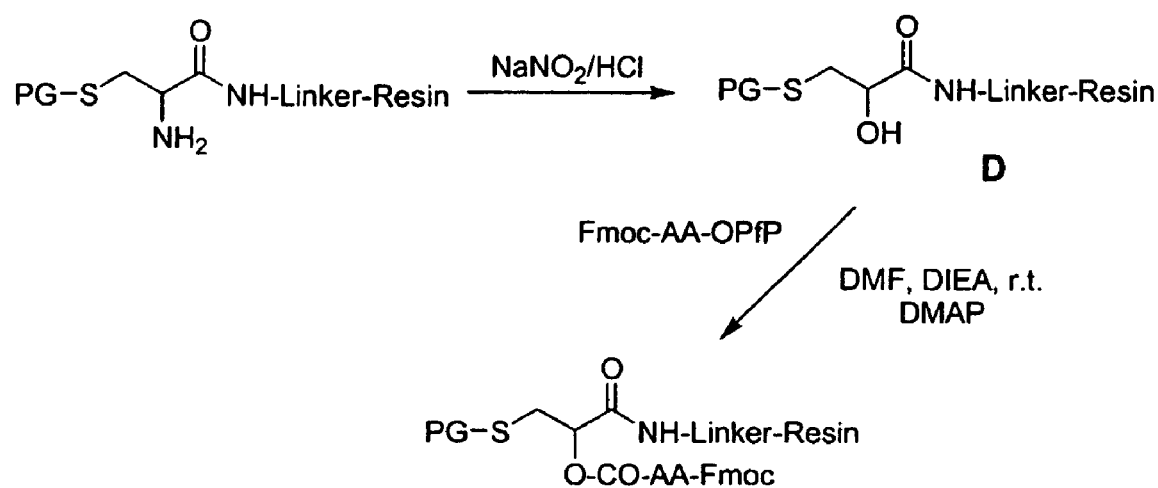

Preparation of Peptide-COO—CH(—CH$_2$—S—S-t-But)CONH$_2$ (FIG. 10D)

PEGA amino resin (0.2 mmol) was swollen in DMF. The resin was treated with a solution 10% DIEA in DMF (2×2 min), then it was washed with DMF. Fmoc Rink linker (MW=539, 2 mmol, 1.08 g) was activated with HBTU/DEA and coupled to the resin. After 1 hour the resin was drained and washed with DMF. The coupling was repeated. After 1 hour the resin was drained and washed with DMF. A resin sample gave negative ninhydrin reaction.

After Fmoc removal with a solution 20% piperidine in DMF (2×3 min), FmocCys(t-Bu-thio)OH (MW=432, 2 mmol, 864 mg) was activated with HBTU/DIEA and coupled to the resin for 1 hour. The resin was drained and washed with DMF. A resin sample gave negative ninhydrin reaction.

After Fmoc removal, the resin was washed with water and it was swollen in water 10 minutes. It was drained then it was suspended in 2 ml of a cold solution 0.5 M of HCl (Harris et al. J. Am. Chem. Soc. 1988, 110, 940-949). 1 ml of a freshly prepared solution of KNO$_2$ 2.8 M (MW=85.11, 238.3 mg) was added at 0° C. dropwise, over 20 minutes, under stirring, to the resin. After the addition it was left reacting 4 hours at room temperature under stirring.

Then the resin was drained, washed with water then with a saturated solution of Na$_2$CO$_3$. It was drained and a fresh solution of Na$_2$CO$_3$ was added. The resin was suspended in this solution for 20 minutes. Then it was drained, washed with water, then with DMF. A resin sample gave negative ninhydrin reaction.

The first Fmoc amino acid (2 mmol) was activated with HBTU/DIEA in the presence of a catalytic amount of DMAP and it was coupled to the resin for 1 hour. A double coupling was necessary. Then the SPPS was performed manually, using 10 excess of each activated Fmoc amino acid and monitored with the ninhydrin test.

After the final cycle the Fmoc was cleaved and the peptide-resin was washed first with DMF then with DCM without drying. It was then suspended in a mixture TFA/TIS/H$_2$O: 90/5/5 under stirring at room temperature. After 1 h 30 the resin was removed by filtration and washed with TFA. Diethyl ether was added and the solid was collected by filtration, washed with diethyl ether and dried in vacuo.

Example 6

Preparation of Peptide-COOCH(—CH$_2$—SH) CONH$_2$ via BrH$_2$COCOOH

Rink amide resin (Novabiochem 0.61 mmol/g, 0.18 mmol, 300 mg) was swollen in DMF for 10 minutes, then it was washed with DMF. After Fmoc removal with a solution 20% of Piperidine in DMF (2×3 min), Bromo pyruvic acid (MW=166.96, 1.8 mmol, 300 mg)) was activated with 1.5 eq of DCC (MW=206.33, 2.7 mmol, 557 mg) and 2 eq. of N-hydroxysuccinimide (MW=115.09, 3.6 mmol, 414 mg) in 3.6 ml of DMF for 20 minutes, then the mixture was added to the resin. After 3 hours the resin was drained and washed with DMF. A sample of resin gave negative ninhydrin reaction.

The resin was treated with a solution of Triphenylmethyl mercaptan (MW=276.40, 0.9 mmol, 249 mg) and DIEA (MW=129.25, d=0.742, 0.9 mmol, 156 μl) in 1.8 ml of DMF for 1 hour. Then it was drained, washed with DMF and successively with THF. The resin was suspended in THF for 10 minutes, then it was treated overnight with a solution of $LiBH_4$ (MW=21.78, 0.5 mmol, 11.8 mg) in 1.1 ml of THF. The resin was drained, washed with THF, then with DMF.

The first Fmoc amino acid was activated with DCC and DMAP and coupled to the resin for 2 hours. The coupling was repeated for 1 hour. Then, the SPPS proceeded with the usual activation of the Fmoc amino acids using HBTU/DIEA and it was monitored with the ninhydrin test.

After the final cycle the Fmoc was cleaved, the peptide-resin was washed respectively with DMF, DCM, DCM/MeOH 50/50 and it was dried. It was then treated with a mixture of TFA/TIS/$H_2O$: 90/5/5 under stirring at room temperature After 1 h 30 the resin was removed by filtration and washed with TFA. Diethyl ether was added and the solid was collected by filtration, washed with diethyl ether and dried in vacuo.

Example 7

Ligation Multistep-LYRAN-COSR[6] (SEQ ID NO: 4)+CLYRAFCOOCH(—$CH_2$—S—S-t-But)$CONH_2$ (SEQ ID NO: 5)+CYAKYAKL (SEQ ID NO: 6) (FIGS. 8a to 8d)

0.30 mg of LYRAN-COSR[6] (SEQ ID NO: 4) (MW=822, 0.36 μmol) and 0.35 mg of CLYRAFCOOCH($CH_2$—S—S-t-But)$CONH_2$ (SEQ ID NO: 5) (MW=963, 0.36 μmol) were dissolved in 60 μl of ligation buffer (6M Guanidine.HCl, 0.2M sodium phosphate, pH=7.5) (FIG. 8a).

To the mixture was added 1 μl of a stock solution of thiophenol (1 μl of thiophenol+7 μl of ligation buffer) to have 0.2% of thiophenol. The pH was then adjusted at 6.5. The reaction was almost finished after 1 hour, over 90% (FIGS. 8b and 8c, after 1 h).

1.5 eq of CYAKYAKL(SEQ ID NO: 6) (MW=958, 0.51 mg) and 0.9 μl of thiophenol (2% in total) were added to the ligation mixture and the pH was adjusted at 6.5 (FIG. 8d, showing the first ligation after 1 h, overlayed with a time course (1 h, 4 h and overnight) of the second ligation).

Example 8

Ligation of LYRAFCOO—CH(—$CH_2$—S—S-t-But)-$CONH_2$ (SEQ ID NO: 1)+CYAKYAKL (SEQ ID NO: 6) (FIG. 11) and of LYRAG(—S—S-t-But) (SEQ ID NO: 2)+CYAKYAKL (SEQ ID NO: 6) (FIG. 12)

Figure 11:
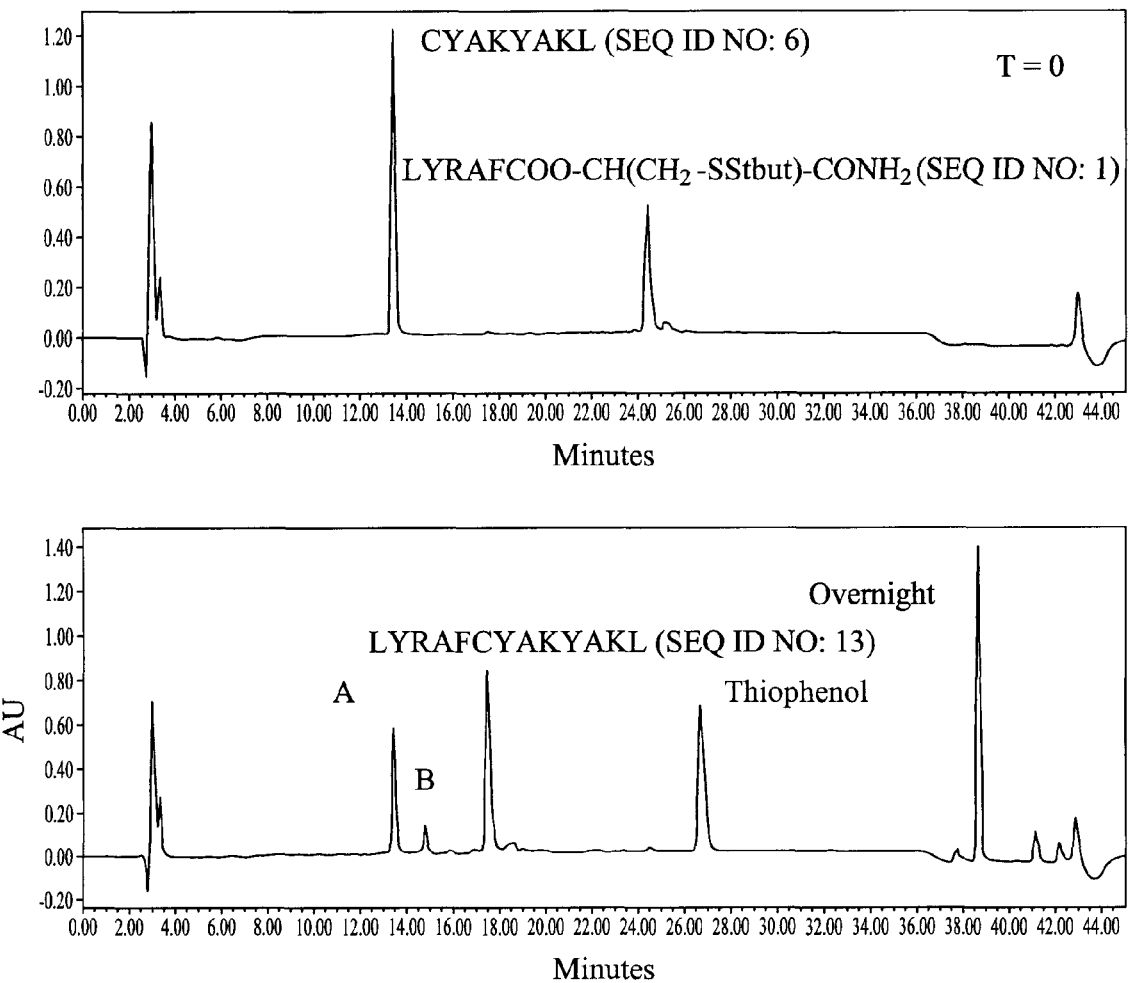
FIG. 11 illustrates the ligation of model Peptide LYRAF-COO—CH(CH$_2$—S—S-t-But)-CONH$_2$ (SEQ ID NO: 1) at time=0 and after overnight reaction. 'LYRAF', 'CYAKY-AKL', and 'LYRAFCYAKYAKL' are disclosed as SEQ ID NOS 1, 6 and 13, respectively.

These two additional exemplary ligation reactions are depicted in FIG. 11 (for LYRAFCOO—CH($CH_2$—SStbut)-$CONH_2$ (SEQ ID NO: 1)+CYAKYAKL (SEQ ID NO: 6), at T=0 and after overnight reaction) and in FIG. 12 (for LYRAG (-S—S-t-Bu) (SEQ ID NO: 2)+CYAKYAKL (SEQ ID NO: 6), at T=0, and after 4 hours and overnight reaction with 2% Thiophenol at pH 6.5, 2% Thiophenol+1% Benzylmercaptan at pH 6.5, and 2% Thiophenol +2% Tributylphosphine at pH 6.5).

Example 9

Figure 9:
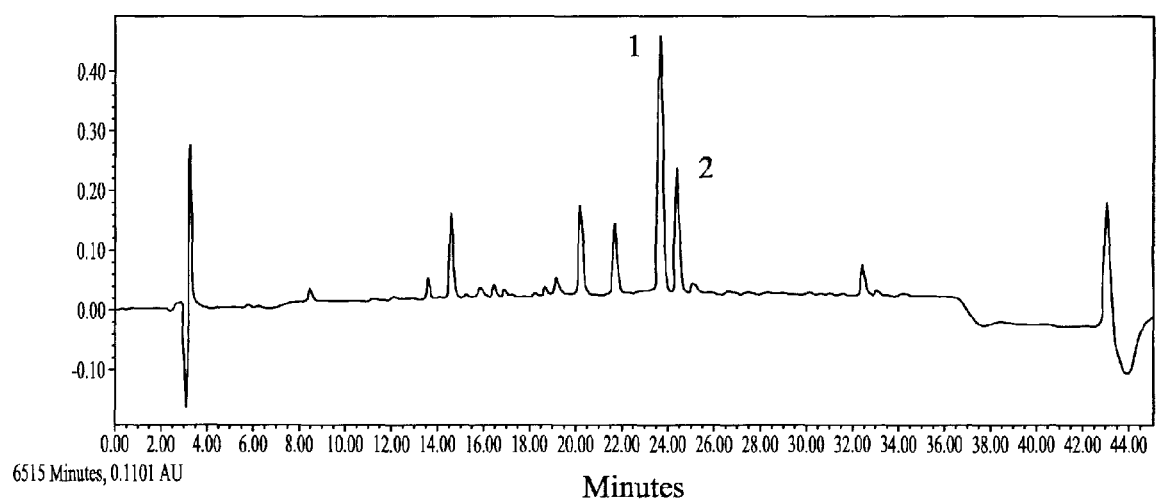
FIG. 9 shows the separation on a cleavage of crude material of the two diastereomers at the C-1 position of the carboxythioester of the present invention. 'LYRAF' is disclosed as SEQ ID NO: 1.

HPLC crude of cleavage of LYRAF(-S—S-t-But) (SEQ ID NO: 1) (FIG. 9)

The synthesis of the model peptide LYRAF-COO—CH ($CH_2$—S—STbut)-CO—$NH_2$ (SEQ ID NO: 1) allowed the separation of 2 peaks with different relative abundance: peak 1 (diastereomer 1) was 68.5% and peak 2 (diastereomer 2) was 31.5% of the desired material, with identical Ms (FIG. 9). Each diastereomers was purified and ligated under the same conditions with an N-terminal Cysteine peptide: the diastereomer 1 gave 17.5% of hydrolyzed product, while the diastereomer 2 (low abundant isomer) gave 13.8% of hydrolyzed product. Therefore the more instable product is the predominant one (diastereomer 1). This demonstrates the utility of the usage of enantiomerically pure compound over the racemate to decrease the side reaction. Indeed, even moderate improvements on small model peptide where the ligation is generally very fast may lead to a more significant difference during slower ligation on larger fragments.

Example 10

Ligation NnyRantes+C-Rantes (FIGS. 13 and 14)

With Tributylphosphine. 3 mg of Nny-Rantes (MW=4016, 0.75 μmol) and 3 mg of C-Rantes (MW=4097, 0.73 μmol) are dissolved in 200 μl of ligation buffer (6M Guanidine.HCl, 0.2M sodium phosphate, pH=7.5). To the mixture are added successively 2% (4 μl) of Thiophenol and 10 μl of a solution Tributylphosphine/Isopropanol (50 μl/50 μl). The pH is then adjusted at 7.00. FIG. 13 depicts the reaction at T=0 and after 2.5 hours (reaction 1).

Without Tributylphosphine. 0.4 mg of Nny-Rantes (MW=4016, 0.01 μmol) and 0.4 mg of C-Rantes (MW=4097, 0.098 μmol) are dissolved in 100 μl of ligation buffer (6M Guanidine.HCl, 0.2M sodium phosphate, pH=7.5). 2% (2 μl) of Thiophenol is added to the mixture and the pH is adjusted at 7.00. FIG. 13 depicts the reaction at T=0 and after 16 hours (reaction 2).

Example 11

Evaluation of Various Electron-Withdrawing Groups

A number of alternative electron-withdrawing groups have been tested for their ability to increase the yields of the ligation reaction. Typically, the yields were measured as the ratio, in percentage, of the hydrolysis product (Pep1COOH) to the ligated product. In order to minimize side-reactions, the group providing the minimal ratio is selected.

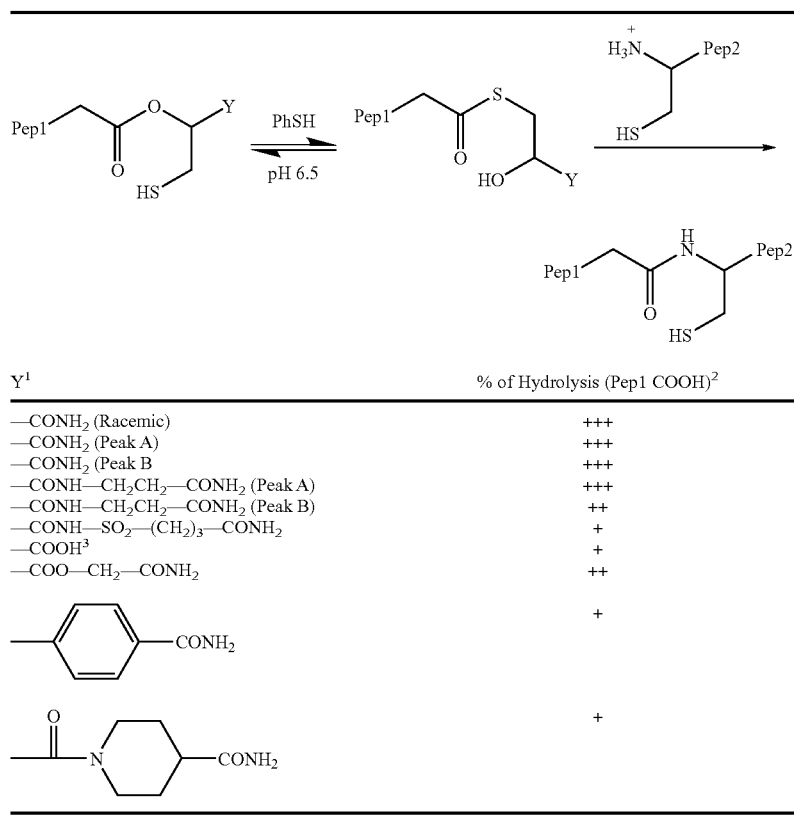

| $Y^1$ | % of Hydrolysis (Pep1 COOH)[2] |
|---|---|
| —$CONH_2$ (Racemic) | +++ |
| —$CONH_2$ (Peak A) | +++ |
| —$CONH_2$ (Peak B) | +++ |
| —CONH—$CH_2CH_2$—$CONH_2$ (Peak A) | +++ |
| —CONH—$CH_2CH_2$—$CONH_2$ (Peak B) | ++ |
| —CONH—$SO_2$—$(CH_2)_3$—$CONH_2$ | + |
| —COOH[3] | + |
| —COO—$CH_2$—$CONH_2$ | ++ |
| phenyl-$CONH_2$ | + |
| piperidinyl-$CONH_2$ | + |

[1] Peptide 1 = LYRAF (SEQ ID NO: 1); Peptide 2 = CYAKYAKL (SEQ ID NO: 6), used in 1.5 eq. Ligation conditions: pH 6.5 phosphate buffer, 2% thiophenol (v/v).
[2] % of Hydrolysis (Pep1COOH) ratio relative to the ligated product as measured by HPLC with UV detection at 214 nm. Hydrolysis of <100%, +; <50%, ++; and <25%, +++.
[3] Model peptide used is LYRAK (SEQ ID NO: 7)

Example 12

Synthesis of Phosphorylated Spermatid Nuclear Transition Protein 1

Spermatid nuclear transition protein 1, (SPT1, Swiss Prot accession P22613) is a 54 residue protein present in sheep sperm and reported to be phosphorylated. One of the phosphorylated sites is serine in position eight. To obtain the full length protein, with the following sequence: STSRKLKS(PO_3H_2)QGTRRGKNRTPHKGVKRGCSKRKYRKSS-LKSRKRCDDANRNFR SHL (SEQ ID NO: 8) Fragment 1 was synthesized using standard Fmoc chemistry and protection, at 0.1 mmoles scale, starting from a PEGA resin prepared as for Example 5. The first amino acid on the resin after the linker, glycine, 10 equivalent to the resin substitution, was introduced as HBTU/DIAE activated ester in presence of 0.1 equivalents of DMAP. Serine in position 8 was introduced as the phosphorylated protected residue FmocSer(PO(OBzl)O-H)OH (commercially available). Cleavage from the resin was conducted in $TFA/TIS/H_2O$ (95/2.5/2.5).

The intermediate Fragment 1: STSRKLKS(PO_3H_2)QGTR-RGKNRTPHKGVKRG-C$^\alpha$OOCH($CH_2$—S—S-t-butyl)-$CONH_2$ (SEQ ID NO: 9) was purified by preparative RP-HPLC.

Fragment 2: CSKRKYRKSSLKSRKRCDDANRNFRSHL (SEQ ID NO: 10) was prepared by standard Boc chemistry, and after HF cleavage, purified by preparative RP-HPLC. Fragment 1 and Fragment 2 were ligated as follows: 0.5 mg of Fragment 1 (MW 3192.71, 0.015 µmoles) and 1.6 mg of Fragment 2 (MW 3440.98, 0.045 µmoles) were dissolved in 200 µl of ligation buffer, (6 M Guanidine.HCl, 0.2 M Sodium Phosphate, pH=7.5). 2% (4 µl) of thiophenol was added to the mixture and the pH was adjusted at 6.5. After 12 hours the ligation solution was analyzed by RP-HPLC and by Size exclusion chromatography. RP-HPLC confirmed the disappearance of Fragment 1. Collection of the major peak and analysis by mass spectroscopy confirmed the co-elution of Fragment 2 and the ligated product. The hydrolyzed Fragment 1 was estimated to represent 12.5% of the initial ester form. (FIG. 15). Size exclusion chromatography was used to resolve the non-reacted Fragment 2 from the full-length material and for the purification of the final material. (FIG. 16). Mass spectroscopy confirmed the nature of the two products. (FIG. 17).

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:

1. A method for preparing an oligopeptide or polypeptide product, comprising:

(a) ligating in a first reaction, first and second oligopeptides each having an N-terminus and a C-terminus, wherein said first oligopeptide comprises a C-terminus having a thioester group, and an N-terminus that is substantially unreactive with said thioester group, wherein said second oligopeptide comprises an N-terminus having an unprotected cysteine, an unprotected 1,2-amino thiol, or an unprotected 1,3-amino thiol, and a C-terminus having an inactive thioester precursor, and wherein said ligating forms a first oligopeptide ligation product comprising a C-terminus having an inactive thioester precursor, and an N-terminus that is substantially unreactive with said thioester group;

(b) ligating in a second reaction, third and fourth oligopeptides each having an N-terminus and a C-terminus, wherein said third oligopeptide comprises an N-terminus having a protected cysteine, a protected 1,2-amino thiol, or a protected 1,3-amino thiol, and a C-terminus comprising a thioester, wherein said fourth oligopeptide comprises an N-terminus having an unprotected cysteine, an unprotected 1,2-amino thiol, or an unprotected 1,3-amino thiol, and a C-terminus that is substantially unreactive with said unprotected cysteine, said unprotected 1,2-amino thiol, or said unprotected 1,3-amino thiol, and wherein said ligating forms a second oligopeptide ligation product comprising an N-terminus having a protected cysteine, a protected 1,2-amino thiol, or a protected 1,3-amino thiol, and a C-terminus that is substantially unreactive with said unprotected cysteine, said unprotected 1,2-amino thiol, or said unprotected 1,3-amino thiol;

(c) transforming said inactive thioester precursor of said first oligopeptide ligation product of step (a) into a thioester to form a third oligopeptide ligation product having a C-terminus comprising a thioester, and an N-terminus that is substantially unreactive with said thioester group;

(d) deprotecting said N-terminus of said second oligopeptide ligation product of step (b) to form a fourth ligation product comprising an N-terminus having an unprotected cysteine, an unprotected 1,2-amino thiol, or an unprotected 1,3-amino thiol, and a C-terminus that is substantially unreactive with said unprotected cysteine, said unprotected 1,2-amino thiol, or said unprotected 1,3-amino thiol; and (e) ligating said third oligopeptide ligation product of step (c) to said fourth oligopeptide ligation product of step (d) to form a fifth oligopeptide ligation product comprising an N-terminus that is substantially unreactive with an oligopeptide bearing a C-terminal thioester group, and a C-terminus that is substantially unreactive with an oligopeptide bearing an unprotected N-terminal cysteine, an unprotected 1,2-amino thiol, or an unprotected 1,3-amino thiol, wherein:

said inactive thioester precursor at said C-terminus is defined by the formula:

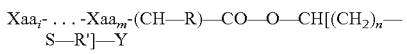

wherein:

$Xaa_i$ is a protected or unprotected amino acid for i=1 to m;
m is an integer from 2 to 200;
n is an integer from 1 to 10;
R is an amino acid side chain;
R' is a member selected from the group consisting of a sulfur protecting group and —SR";
R" is a member selected from the group consisting of $C_{2-10}$alkyl, substituted aryl having from 5 to 12 carbon atoms, substituted benzyl, and substituted heteroaryl having from 5 to 12 carbon atoms and 1 to 4 heteroatoms each independently selected from the group consisting of N, O and S;
Y is an electron withdrawing group selected from the group consisting of $R^c$, $C_{1-3}$alkyl substituted with 1-3 $R^c$ groups, —C(O)—$R^d$, —S(O)p-$C_{1-3}$alkyl substituted with 0-3 $R^c$ groups, and an aryl substituted with 1-3 $R^c$ groups;

each $R^c$ group is independently a member selected from the group consisting of halogen, polyhaloalkyl, substituted or unsubstituted benzyl, substituted or unsubstituted aryl, —C(O)NH$_2$, —C(O)—NHNH$_2$, —S(O)$_2$NH$_2$, substituted and unsubstituted hydroxyl-amine, cyano, nitro and quaternary ammonium salts;
p is an integer from 1 to 2;
$R^d$ is a member selected from the group consisting of hydrogen, N($R^e$)$_2$, —OR$^e$ and —SR$^e$;
each $R^e$ is independently a member selected from the group consisting of hydrogen, $C_{1-3}$alkyl substituted with 0-3 $R^c$ groups, and —SO$_2$—$C_{1-3}$alkyl substituted with 1-3 $R^c$ groups; alternatively,
when two $R^e$ groups are present, they can be taken together with the atom to which they are attached to form a 5-6 membered non-aromatic heterocylic ring containing 1-3 heteroatoms each independently selected from the group consisting of N, O and S, substituted with 0-3 $R^c$ groups.

2. The method of claim 1 further comprising: (f) ligating said fifth oligopeptide ligation product of step (e) to one or more additional oligopeptides, with the proviso that said fifth oligopeptide ligation product of step (e) and said one or more additional oligopeptides bear, or are prepared to bear N-terminal and C-terminal groups capable of chemical ligation, wherein said N-terminal group capable of chemical ligation comprises an unprotected cysteine, an unprotected 1,2-amino thiol, or an unprotected 1,3-amino thiol, and wherein said C-terminal group capable of chemical ligation comprises a thioester.

3. The method of claim 2 wherein Y is —C(O)NH$_2$.

4. The method of claim 1 wherein said N-terminus of said fifth oligopeptide ligation product of step (e) comprises an unprotected N-terminal amino acid, or a protected N-terminal amino acid.

5. The method of claim 4 wherein said protected N-terminal amino acid is cyclic.

6. The method of claim 4 wherein said protected N-terminal amino acid comprises a protected cysteine, a protected 1,2-amino thiol, or a protected 1,3-amino thiol.

7. The method of claim 1 wherein said C-terminus of said fifth oligopeptide ligation product of step (e) comprises an unprotected amino acid, or an inactive thioester precursor.

8. The method of claim 1 wherein R' is a sulfur protecting group.

9. The method of claim 1 wherein R' is —SR".

10. The method of claim 1 wherein R" is a member selected from the group consisting of ethyl, t-butyl and substituted phenyl.

11. The method of claim 1 wherein each step is performed in a solution selected from the group consisting of an organic solvent and an organic and aqueous solvent mixture.

* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Tyr Arg Ala Phe
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Tyr Arg Ala Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Lys Leu Leu Met
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Tyr Arg Ala Asn
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Leu Tyr Arg Ala Phe
1               5

<210> SEQ ID NO 6
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Cys Tyr Ala Lys Tyr Ala Lys Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Tyr Arg Ala Lys
1               5

<210> SEQ ID NO 8
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ser Thr Ser Arg Lys Leu Lys Ser Gln Gly Thr Arg Arg Gly Lys Asn
1               5                   10                  15

Arg Thr Pro His Lys Gly Val Lys Arg Gly Cys Ser Lys Arg Lys Tyr
                20                  25                  30

Arg Lys Ser Ser Leu Lys Ser Arg Lys Arg Cys Asp Asp Ala Asn Arg
            35                  40                  45

Asn Phe Arg Ser His Leu
        50

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Thr Ser Arg Lys Leu Lys Ser Gln Gly Thr Arg Arg Gly Lys Asn
1               5                   10                  15

Arg Thr Pro His Lys Gly Val Lys Arg Gly
                20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Ser Lys Arg Lys Tyr Arg Lys Ser Ser Leu Lys Ser Arg Lys Arg
1               5                   10                  15

Cys Asp Asp Ala Asn Arg Asn Phe Arg Ser His Leu
                20                  25
```

-continued

```
<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Tyr Arg Ala Asn Cys Leu Tyr Arg Ala Phe
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Tyr Arg Ala Asn Cys Leu Tyr Arg Ala Phe Cys Tyr Ala Lys Tyr
1               5                   10                  15

Ala Lys Leu

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Tyr Arg Ala Phe Cys Tyr Ala Lys Tyr Ala Lys Leu
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Tyr Arg Ala Gly Cys Tyr Ala Lys Tyr Ala Lys Leu
1               5                   10
```